US007985404B1

(12) United States Patent
Seiberg et al.

(10) Patent No.: US 7,985,404 B1
(45) Date of Patent: Jul. 26, 2011

(54) REDUCING HAIR GROWTH, HAIR FOLLICLE AND HAIR SHAFT SIZE AND HAIR PIGMENTATION

(75) Inventors: Miri Seiberg, Princeton, NJ (US); Stanley S. Shapiro, Livingston, NJ (US); Jue-Chen Liu, Belle Mead, NJ (US); Jonathan Miller, Lawrenceville, NJ (US)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 0 days.

(21) Appl. No.: 09/621,565

(22) Filed: Jul. 21, 2000

Related U.S. Application Data

(60) Provisional application No. 60/145,774, filed on Jul. 27, 1999.

(51) Int. Cl.
A61Q 5/00 (2006.01)
A61K 38/43 (2006.01)
A61K 8/02 (2006.01)
A61K 36/00 (2006.01)

(52) U.S. Cl. ....... 424/70.1; 424/401; 424/725; 424/94.1
(58) Field of Classification Search .................. 424/401, 424/725, 70.1, 94.1; 514/880
See application file for complete search history.

(56) References Cited

U.S. PATENT DOCUMENTS

| 2,876,164 | A | 3/1959 | Wershaw |
| 2,924,525 | A | 2/1960 | Kruse et al. |
| 3,097,947 | A | 7/1963 | Kemmerer |
| 3,625,976 | A | 12/1971 | Theimer |
| 3,755,560 | A | 8/1973 | Dickert et al. |
| 4,007,266 | A | 2/1977 | Choay |
| 4,056,637 | A | 11/1977 | Hagiwara et al. |
| 4,151,304 | A | 4/1979 | Evans |
| 4,190,671 | A | 2/1980 | Vanstone et al. |
| 4,219,569 | A | 8/1980 | Glenn |
| 4,223,018 | A | 9/1980 | Belle |
| 4,254,105 | A | 3/1981 | Fukuda |
| 4,272,544 | A | 6/1981 | Cella et al. |
| 4,278,570 | A | 7/1981 | Flom |
| 4,279,930 | A | 7/1981 | Hall et al. |
| 4,297,348 | A | 10/1981 | Frazier |
| 4,331,692 | A | 5/1982 | Drevici et al. |
| 4,333,927 | A | 6/1982 | Ofuchi et al. |
| 4,368,187 | A | 1/1983 | Flom et al. |
| 4,370,315 | A | 1/1983 | Greff et al. |
| 4,382,960 | A | 5/1983 | Flom |
| 4,386,067 | A | 5/1983 | Guillon |
| 4,421,769 | A | 12/1983 | Dixon et al. |

(Continued)

FOREIGN PATENT DOCUMENTS

AU 1998/70006 B2 5/1998
(Continued)

OTHER PUBLICATIONS

Itami, et al. Mechanism of Action of Androgen in Hair Follicles, Journal of Dermatological Science, 7 Supp., S98-103, Jul. 1994.

(Continued)

Primary Examiner — Blessing M Fubara

(57) ABSTRACT

The present invention utilizes natural and/or synthetic serine protease inhibitory agents or botanical extracts containing serine protease inhibitory activity, with or without the addition of one or more isoflavones and/or additional natural extracts containing one or more isoflavones, and their ability to affect changes in mammalian hair growth, hair follicle and hair shaft size and hair pigmentation.

30 Claims, 18 Drawing Sheets

U.S. PATENT DOCUMENTS

| | | |
|---|---|---|
| 4,427,670 A | 1/1984 | Ofuchi et al. |
| 4,434,095 A | 2/1984 | Chipens et al. |
| 4,437,895 A | 3/1984 | Koulbanis et al. |
| 4,439,418 A | 3/1984 | Möller et al. |
| 4,462,981 A | 7/1984 | Smith |
| 4,477,434 A | 10/1984 | Kosaka |
| 4,486,448 A | 12/1984 | Ser et al. |
| 4,488,564 A | 12/1984 | Grollier et al. |
| 4,512,973 A | 4/1985 | Dennis |
| 4,515,778 A | 5/1985 | Kastell |
| 4,524,067 A | 6/1985 | Arichi et al. |
| 4,537,782 A | 8/1985 | Millet et al. |
| 4,550,035 A | 10/1985 | Smith |
| 4,578,267 A | 3/1986 | Salamone |
| 4,584,190 A | 4/1986 | Tejima et al. |
| 4,603,146 A | 7/1986 | Kligman |
| 4,604,281 A | 8/1986 | Deckner et al. |
| 4,612,192 A | 9/1986 | Scheuffgen et al. |
| 4,690,821 A | 9/1987 | Smith et al. |
| 4,707,293 A | 11/1987 | Ferro |
| 4,727,088 A | 2/1988 | Scott et al. |
| 4,760,096 A | 7/1988 | Sakai et al. |
| 4,793,991 A | 12/1988 | Slimak |
| 4,824,662 A | 4/1989 | Hofmann |
| 4,834,076 A | 5/1989 | Millet et al. |
| 4,847,267 A | 7/1989 | Deckner et al. |
| 4,851,214 A | 7/1989 | Walters et al. |
| 4,859,458 A | 8/1989 | Salamone et al. |
| 4,867,964 A | 9/1989 | Forestier et al. |
| 4,871,530 A | 10/1989 | Grollier et al. |
| 4,885,169 A | 12/1989 | Gazzani |
| 4,895,839 A | 1/1990 | Bombardelli |
| 4,906,457 A | 3/1990 | Ryan |
| 4,943,462 A | 7/1990 | Komerska et al. |
| 4,960,588 A | 10/1990 | Hoshowski et al. |
| 4,960,764 A | 10/1990 | Figueroa, Jr. et al. |
| 4,970,216 A | 11/1990 | Deckner et al. |
| 4,971,825 A | 11/1990 | Kitazume et al. |
| 4,978,528 A | 12/1990 | Degre |
| 5,002,761 A | 3/1991 | Mueller et al. |
| 5,006,337 A | 4/1991 | Motitschke et al. |
| 5,032,382 A | 7/1991 | Grollier |
| 5,032,400 A | 7/1991 | Wiersum et al. |
| 5,043,323 A | 8/1991 | Bombardelli et al. |
| 5,057,417 A | 10/1991 | Hammonds et al. |
| 5,077,038 A | 12/1991 | Hofmann |
| 5,077,040 A | 12/1991 | Bergmann et al. |
| 5,104,655 A | 4/1992 | Bombardelli et al. |
| 5,110,603 A | 5/1992 | Rau |
| 5,116,605 A | 5/1992 | Alt |
| 5,118,671 A | 6/1992 | Bombardelli et al. |
| 5,130,142 A | 7/1992 | Wong et al. |
| 5,147,859 A | 9/1992 | Bombardelli et al. |
| 5,166,139 A | 11/1992 | Bombardelli et al. |
| 5,171,577 A | 12/1992 | Griat et al. |
| 5,179,091 A | 1/1993 | Lesieur et al. |
| 5,188,823 A | 2/1993 | Shapiro et al. |
| 5,192,332 A | 3/1993 | Lang et al. |
| 5,194,252 A | 3/1993 | Hofmann |
| 5,217,717 A | 6/1993 | Kennedy et al. |
| 5,229,104 A | 7/1993 | Sottery et al. |
| 5,231,090 A | 7/1993 | Hsia |
| 5,248,495 A | 9/1993 | Patterson et al. |
| 5,254,331 A | 10/1993 | Mausner |
| 5,260,065 A | 11/1993 | Mathur et al. |
| 5,270,042 A | 12/1993 | Whitham |
| 5,276,058 A | 1/1994 | Satoh et al. |
| 5,304,482 A * | 4/1994 | Sambrook et al. ............ 435/226 |
| 5,306,444 A | 4/1994 | Kitamura et al. |
| 5,310,734 A | 5/1994 | Losch et al. |
| 5,322,839 A | 6/1994 | Voegeli |
| 5,352,443 A | 10/1994 | Kubo et al. |
| 5,362,494 A | 11/1994 | Zysman et al. |
| 5,364,886 A | 11/1994 | Löliger et al. |
| 5,393,519 A | 2/1995 | Dowell et al. |
| 5,397,497 A | 3/1995 | Jakobson et al. |
| 5,407,675 A | 4/1995 | Etemad-Moghadam |
| 5,411,742 A | 5/1995 | Sebag |
| 5,427,814 A | 6/1995 | Löliger |
| 5,428,026 A | 6/1995 | Colarow |
| 5,438,044 A | 8/1995 | Losch et al. |
| 5,439,672 A | 8/1995 | Zabotto et al. |
| 5,443,839 A | 8/1995 | Meybeck |
| 5,443,840 A | 8/1995 | Morancais et al. |
| 5,444,092 A | 8/1995 | Collins |
| 5,446,605 A | 8/1995 | Umehara |
| 5,466,452 A | 11/1995 | Whittle |
| 5,468,473 A | 11/1995 | Mullen |
| 5,498,420 A | 3/1996 | Mentrup Edgar et al. |
| 5,503,832 A | 4/1996 | De Stoutz |
| 5,505,946 A | 4/1996 | Kennedy et al. |
| 5,510,391 A | 4/1996 | Elson |
| 5,523,308 A | 6/1996 | Costanzo et al. |
| 5,539,129 A | 7/1996 | Zysman et al. |
| 5,545,399 A | 8/1996 | Lee et al. |
| 5,547,661 A | 8/1996 | Sun et al. |
| 5,554,647 A | 9/1996 | Perricone |
| 5,565,493 A | 10/1996 | Nakata et al. |
| 5,567,420 A | 10/1996 | McEleney et al. |
| 5,569,663 A | 10/1996 | Ribier et al. |
| 5,571,503 A | 11/1996 | Mausner |
| 5,578,297 A | 11/1996 | Mellul et al. |
| 5,589,181 A | 12/1996 | Bencsits |
| 5,595,984 A | 1/1997 | Blank |
| 5,597,814 A | 1/1997 | Blank |
| 5,601,833 A | 2/1997 | Ribier et al. |
| 5,603,949 A | 2/1997 | Meybeck et al. |
| 5,605,894 A | 2/1997 | Blank |
| 5,607,666 A | 3/1997 | Masson |
| 5,607,692 A | 3/1997 | Ribier et al. |
| 5,614,180 A | 3/1997 | Chung |
| 5,614,215 A | 3/1997 | Ribier et al. |
| 5,616,572 A | 4/1997 | Blank |
| 5,618,522 A | 4/1997 | Kaleta et al. |
| 5,620,692 A | 4/1997 | Potter et al. |
| 5,622,690 A | 4/1997 | Potter et al. |
| 5,626,868 A | 5/1997 | Morancais et al. |
| 5,629,015 A | 5/1997 | Ribier et al. |
| 5,629,301 A | 5/1997 | Blank |
| 5,631,318 A | 5/1997 | Ito et al. |
| 5,635,165 A | 6/1997 | Panitch |
| 5,637,316 A | 6/1997 | Ribier et al. |
| 5,639,785 A | 6/1997 | Kung |
| 5,641,509 A | 6/1997 | Gross et al. |
| 5,643,583 A | 7/1997 | Voultoury et al. |
| 5,643,587 A | 7/1997 | Scancarella et al. |
| 5,643,601 A | 7/1997 | Gross et al. |
| 5,650,166 A | 7/1997 | Ribier et al. |
| 5,652,230 A | 7/1997 | Blank |
| 5,653,988 A | 8/1997 | Gerber et al. |
| 5,660,853 A | 8/1997 | Hansenne-Richoux |
| 5,665,367 A | 9/1997 | Burger et al. |
| 5,670,547 A | 9/1997 | Milstein et al. |
| 5,674,511 A | 10/1997 | Kacher et al. |
| 5,676,935 A | 10/1997 | Mellul et al. |
| 5,676,956 A | 10/1997 | Duffy et al. |
| 5,679,374 A | 10/1997 | Fanchon et al. |
| 5,681,571 A | 10/1997 | Horngren et al. |
| 5,681,852 A | 10/1997 | Bissett |
| 5,683,380 A | 11/1997 | Eckhouse et al. |
| 5,683,683 A | 11/1997 | Scafidi |
| 5,686,102 A | 11/1997 | Gross et al. |
| 5,688,763 A | 11/1997 | Hammonds, Jr. et al. |
| 5,691,327 A | 11/1997 | Blank |
| 5,712,356 A | 1/1998 | Bothe et al. |
| 5,720,772 A | 2/1998 | Eckhouse |
| 5,723,148 A | 3/1998 | Love |
| 5,741,496 A | 4/1998 | Khaiat |
| 5,753,612 A | 5/1998 | Mitrani |
| 5,755,814 A | 5/1998 | Berg et al. |
| 5,762,916 A | 6/1998 | Ansmann et al. |
| 5,766,628 A | 6/1998 | Nürnberg et al. |
| 5,776,917 A | 7/1998 | Blank et al. |
| 5,780,456 A | 7/1998 | Blank |
| 5,780,457 A | 7/1998 | Blank |
| 5,780,458 A | 7/1998 | Blank |
| 5,780,459 A | 7/1998 | Blank et al. |

| | | | | | | |
|---|---|---|---|---|---|---|
| 5,786,345 A | 7/1998 | Blank et al. | 6,272,883 B2 | 8/2001 | Bruder et al. | |
| 5,786,346 A | 7/1998 | Blank | 6,273,885 B1 | 8/2001 | Koop et al. | |
| 5,789,396 A | 8/1998 | Blank et al. | 6,323,219 B1 * | 11/2001 | Costanzo | 514/317 |
| 5,795,879 A | 8/1998 | Blank | 6,358,242 B1 | 3/2002 | Cecchetti | |
| 5,801,163 A | 9/1998 | Blank | 6,365,802 B2 * | 4/2002 | Kridl | 800/312 |
| 5,804,216 A | 9/1998 | Terren et al. | 6,399,083 B1 | 6/2002 | Pillai et al. | |
| 5,807,545 A | 9/1998 | Coffindaffer et al. | 6,413,546 B1 | 7/2002 | He et al. | |
| 5,824,702 A | 10/1998 | Wei | 6,423,747 B1 | 7/2002 | Lanzendörfer | |
| 5,833,965 A | 11/1998 | Sun et al. | 6,433,025 B1 | 8/2002 | Lorenz | |
| 5,834,013 A | 11/1998 | Ribier et al. | 6,447,809 B1 | 9/2002 | Krumhar et al. | |
| 5,834,513 A | 11/1998 | Ptchelintsev | 6,461,348 B1 | 10/2002 | Bertan et al. | |
| 5,840,717 A | 11/1998 | Blank | 6,461,627 B1 | 10/2002 | Ichioka | |
| 5,843,907 A | 12/1998 | Sakai et al. | 6,485,484 B1 | 11/2002 | Connors et al. | |
| 5,843,926 A | 12/1998 | Blank | 6,544,255 B2 | 4/2003 | Stewart | |
| 5,863,546 A | 1/1999 | Swinehart | 6,551,606 B1 | 4/2003 | Golz-Berner et al. | |
| 5,869,031 A | 2/1999 | Tarroux et al. | 6,558,656 B2 | 5/2003 | Mann | |
| 5,869,470 A | 2/1999 | Blank et al. | 2002/0034489 A1 | 3/2002 | Wiegland | |
| 5,871,480 A | 2/1999 | Tankovich | 2002/0035046 A1 | 3/2002 | Lukenbach | |
| 5,871,743 A | 2/1999 | Chajuss | 2002/0065300 A1 | 5/2002 | Seiberg et al. | |
| 5,871,823 A | 2/1999 | Anders et al. | 2002/0160061 A1 | 10/2002 | Saliou et al. | |
| 5,880,314 A | 3/1999 | Shinomiya et al. | 2002/0160062 A1 | 10/2002 | Liu et al. | |
| 5,885,593 A | 3/1999 | Epstein | 2002/0160063 A1 | 10/2002 | Miller et al. | |
| 5,885,596 A | 3/1999 | Parab | 2002/0182166 A1 | 12/2002 | Martin | |
| 5,885,600 A | 3/1999 | Blum et al. | 2002/0192313 A1 | 12/2002 | Saliou et al. | |
| 5,885,617 A | 3/1999 | Jordan | 2002/0197244 A1 | 12/2002 | Seiberg et al. | |
| 5,885,948 A | 3/1999 | Glenn, Jr. et al. | 2003/0064049 A1 | 4/2003 | Seiberg et al. | |
| 5,888,522 A | 3/1999 | Pickart | 2003/0224075 A1 | 12/2003 | Liu et al. | |
| 5,908,618 A | 6/1999 | Lorant | 2004/0009142 A1 | 1/2004 | Zambaux et al. | |
| 5,912,175 A | 6/1999 | Wille, Jr. | 2004/0062731 A1 | 4/2004 | Seiberg et al. | |
| 5,916,577 A | 6/1999 | Golz et al. | 2004/0063593 A1 | 4/2004 | Wu et al. | |
| 5,928,654 A | 7/1999 | Duranton | 2004/0067244 A1 | 4/2004 | Friedman | |
| 5,928,658 A | 7/1999 | Kishida et al. | 2005/0008665 A1 | 1/2005 | Batzer | |
| 5,928,889 A | 7/1999 | Bakich et al. | 2005/0019279 A1 | 1/2005 | Goppel | |
| 6,750,229 B2 | 7/1999 | Seiberg et al. | 2005/0281776 A1 | 12/2005 | Courcoux | |
| 5,936,052 A | 8/1999 | Bothe et al. | 2007/0009459 A1 | 1/2007 | Magnant | |
| 5,942,479 A | 8/1999 | Frankenbach et al. | 2007/0041931 A1 | 2/2007 | Morelli | |
| 5,945,095 A | 8/1999 | Mougin et al. | 2007/0160564 A1 | 7/2007 | Liu et al. | |
| 5,945,109 A | 8/1999 | Schmidt et al. | | | | |
| 5,952,373 A | 9/1999 | Lanzendörfer et al. | FOREIGN PATENT DOCUMENTS | | | |
| 5,958,387 A | 9/1999 | Bara et al. | | | | |
| 5,958,946 A * | 9/1999 | Styczynski et al. | CN | 1081899 A | 2/1994 | |
| 5,961,980 A | 10/1999 | Kennedy | CN | 1 094 279 | 11/1994 | |
| 5,962,015 A | 10/1999 | Delrieu et al. | CN | 1146876 A | 4/1997 | |
| 5,962,441 A | 10/1999 | Blank | CN | 1166960 A | 12/1997 | |
| 5,965,153 A | 10/1999 | Allen | DE | 4432947 A | 3/1996 | |
| 5,972,355 A | 10/1999 | Knight et al. | DE | 19634206 A | 3/1998 | |
| 5,981,450 A | 11/1999 | Fabry et al. | DE | 19818849 A | 10/1998 | |
| 5,985,338 A | 11/1999 | Suh et al. | EP | 0421021 | 6/1989 | |
| 5,985,809 A | 11/1999 | Frankenbach et al. | EP | 0 341 745 A1 | 11/1989 | |
| 5,985,842 A * | 11/1999 | Miljkovic ............... 514/23 | EP | 0 393 532 A2 | 10/1990 | |
| 5,990,291 A | 11/1999 | Waggle et al. | EP | 0 476 311 A1 | 3/1992 | |
| 6,004,915 A | 12/1999 | Elliott et al. | EP | 0473502 A1 | 3/1992 | |
| 6,013,250 A | 1/2000 | Cannell et al. | EP | 0 508 886 A1 | 10/1992 | |
| 6,013,255 A | 1/2000 | Edens et al. | EP | 0 532 465 A | 3/1993 | |
| 6,017,549 A | 1/2000 | Knight et al. | EP | 0 574 352 A1 | 12/1993 | |
| 6,017,893 A | 1/2000 | Segelman | EP | 0 581 624 A1 | 2/1994 | |
| 6,018,001 A | 1/2000 | Hiratani et al. | EP | 0 581 624 B1 | 2/1994 | |
| 6,019,962 A | 2/2000 | Rabe et al. | EP | 0 582 239 A1 | 2/1994 | |
| 6,030,931 A | 2/2000 | Vinski et al. | EP | 0 582 239 B1 | 2/1994 | |
| 6,033,680 A | 3/2000 | Dixon et al. | EP | 0 643 083 A1 | 3/1995 | |
| 6,045,548 A | 4/2000 | Furumoto et al. | EP | 0 643 960 A1 | 3/1995 | |
| 6,045,779 A | 4/2000 | Mueller et al. | EP | 0 655 470 A1 | 5/1995 | |
| 6,048,520 A | 4/2000 | Hoshowski | EP | 0273202 B1 | 6/1995 | |
| 6,051,602 A | 4/2000 | Bissett | EP | 0 661 037 A1 | 7/1995 | |
| 6,054,137 A | 4/2000 | Breton et al. | EP | 0707851 A2 | 4/1996 | |
| 6,060,070 A | 5/2000 | Gorbach | EP | 0707851 A3 | 4/1996 | |
| 6,063,398 A | 5/2000 | Gueret | EP | 0 713 106 A1 | 5/1996 | |
| 6,080,393 A | 6/2000 | Liu et al. | EP | 0 758 687 A1 | 2/1997 | |
| 6,093,411 A | 7/2000 | Bissett | EP | 0774249 A2 | 5/1997 | |
| 6,096,327 A | 8/2000 | Lezdey et al. | EP | 0 814 116 A1 | 12/1997 | |
| 6,126,933 A | 10/2000 | Warne et al. | EP | 0811595 A1 | 12/1997 | |
| 6,139,899 A * | 10/2000 | Matsuura et al. ............ 426/634 | EP | 0 963 761 A1 | 12/1999 | |
| 6,180,662 B1 | 1/2001 | Lanzendörfer et al. | EP | 1 074 240 A2 | 2/2001 | |
| 6,183,761 B1 | 2/2001 | Bissett et al. | EP | 1077 063 A2 | 2/2001 | |
| 6,183,762 B1 | 2/2001 | Deckers et al. | EP | 1 192 938 A2 | 4/2002 | |
| 6,555,143 B2 | 2/2001 | Miller et al. | EP | 1 210 946 A | 6/2002 | |
| 6,217,572 B1 | 4/2001 | Tobinick | EP | 1 236 402 A2 | 9/2002 | |
| 6,248,350 B1 | 6/2001 | Mori et al. | EP | 1 236 465 A2 | 9/2002 | |
| 6,261,603 B1 | 7/2001 | McElwain | EP | 1 348 441 A | 10/2003 | |
| | | | EP | 1 647 278 A | 4/2006 | |

| | | | | | | |
|---|---|---|---|---|---|---|
| FR | 2 596 986 A1 | 10/1987 | | KR | 92-8851 | 10/1992 |
| FR | 2 641 696 A1 | 7/1990 | | KR | 92-8853 B | 10/1992 |
| FR | 2 685 202 A1 | 6/1993 | | RU | 2066992 C1 | 9/1996 |
| FR | 2803747 | 7/2001 | | WO | WO 87/07838 A1 | 12/1987 |
| FR | 2 811 226 A1 | 1/2002 | | WO | WO 91/04283 A1 | 4/1991 |
| GB | 1098951 A | 1/1968 | | WO | WO 91/07166 | 5/1991 |
| JP | 58-225003 | 6/1982 | | WO | WO 92/09639 A2 | 6/1992 |
| JP | 58225004 | 12/1983 | | WO | WO 92/09650 A1 | 6/1992 |
| JP | 59187756 A | 10/1984 | | WO | WO 94/06485 A1 | 3/1994 |
| JP | 60061513 A | 4/1985 | | WO | WO 94/07462 A | 4/1994 |
| JP | 63-68512 | 9/1986 | | WO | WO 95/04609 A1 | 2/1995 |
| JP | 6-2036304 A | 2/1987 | | WO | WO 95/09002 A1 | 4/1995 |
| JP | 62 036304 | 2/1987 | | WO | WO 95/09011 A1 | 4/1995 |
| JP | 62036304 A | 2/1987 | | WO | WO 95/24885 A1 | 9/1995 |
| JP | 63-316711 | 6/1987 | | WO | WO 96/09806 A2 | 4/1996 |
| JP | 196106 | 10/1987 | | WO | WO 96/19483 | 6/1996 |
| JP | 63-96120 | 4/1988 | | WO | WO 96/19491 | 6/1996 |
| JP | 63135310 A | 6/1988 | | WO | WO 96/24371 | 8/1996 |
| JP | 63-227515 | 9/1988 | | WO | WO 96/24392 A1 | 8/1996 |
| JP | 1093519 A | 4/1989 | | WO | WO 96/29050 A | 9/1996 |
| JP | 1096106 A | 4/1989 | | WO | WO 96/30035 | 10/1996 |
| JP | 3-127713 | 10/1989 | | WO | WO 96/30396 | 10/1996 |
| JP | 02-286165 A | 11/1990 | | WO | WO 96/31194 | 10/1996 |
| JP | 5-320061 | 5/1991 | | WO | WO 96/37497 | 11/1996 |
| JP | 5-25027 A | 7/1991 | | WO | WO 96/40121 A1 | 12/1996 |
| JP | 5-320024 | 5/1992 | | WO | WO 96/40199 A1 | 12/1996 |
| JP | 4-169514 | 6/1992 | | WO | WO 97/11033 | 3/1997 |
| JP | 04283518 A | 10/1992 | | WO | WO 97/18904 A1 | 5/1997 |
| JP | 5015574 A | 1/1993 | | WO | WO 97/35998 | 10/1997 |
| JP | 5-25027 A * | 2/1993 | | WO | WO 97/39733 A1 | 10/1997 |
| JP | 05025027 A | 2/1993 | | WO | WO 98/01107 A1 | 1/1998 |
| JP | 5114905 A | 5/1993 | | WO | WO 98/02134 | 1/1998 |
| JP | 5-213729 | 8/1993 | | WO | WO 98/02138 A1 | 1/1998 |
| JP | 5-246932 | 9/1993 | | WO | WO 98/05333 | 2/1998 |
| JP | 899891 | 1/1994 | | WO | WO 98/08503 | 3/1998 |
| JP | 6145061 A | 5/1994 | | WO | WO 98/09987 | 3/1998 |
| JP | 7304655 | 5/1994 | | WO | WO 98/17246 A1 | 4/1998 |
| JP | 812560 | 6/1994 | | WO | WO 98/33089 A1 | 7/1998 |
| JP | 8-020597 | 7/1994 | | WO | WO 98/49153 | 11/1998 |
| JP | 6192085 A | 7/1994 | | WO | WO 99/00110 A1 | 1/1999 |
| JP | 06256156 A | 9/1994 | | WO | WO 99/04752 A2 | 2/1999 |
| JP | 6256156 A | 9/1994 | | WO | WO 99/09065 A1 | 2/1999 |
| JP | 7010772 A | 1/1995 | | WO | WO 99/15917 A1 | 4/1999 |
| JP | 925212 | 7/1995 | | WO | WO 99/24003 | 5/1999 |
| JP | 925214 | 7/1995 | | WO | WO 99/30729 A1 | 6/1999 |
| JP | 7196527 A | 8/1995 | | WO | WO 99/36050 | 7/1999 |
| JP | 7196529 A | 8/1995 | | WO | WO 99/39682 A2 | 8/1999 |
| JP | 7304655 | 11/1995 | | WO | WO 99/57178 A1 | 11/1999 |
| JP | 08012531 A | 1/1996 | | WO | WO 00/15188 | 3/2000 |
| JP | 8012560 A | 1/1996 | | WO | WO 00/43049 A1 | 7/2000 |
| JP | 8040824 A | 2/1996 | | WO | WO 00/51554 A2 | 9/2000 |
| JP | 8059450 A | 3/1996 | | WO | WO 00/51554 A3 | 9/2000 |
| JP | 08081336 A | 3/1996 | | WO | WO 00/62740 A2 | 10/2000 |
| JP | 8143442 A | 6/1996 | | WO | WO 00/62740 A3 | 10/2000 |
| JP | 408143442 | 6/1996 | | WO | WO 00/62741 A2 | 10/2000 |
| JP | 8333260 A | 12/1996 | | WO | WO 00/62741 A3 | 10/2000 |
| JP | 09 025212 | 1/1997 | | WO | WO 00/62743 A2 | 10/2000 |
| JP | 9025212 A | 1/1997 | | WO | WO 00/62743 A3 | 10/2000 |
| JP | 9025213 A | 1/1997 | | WO | WO 00/62744 A3 | 10/2000 |
| JP | 9025214 A | 1/1997 | | WO | WO 00/62745 | 10/2000 |
| JP | 090 59166 | 3/1997 | | WO | WO 00162744 A2 | 10/2000 |
| JP | 90 59166 * | 3/1997 | | WO | WO 00/69404 | 11/2000 |
| JP | 9077638 A | 3/1997 | | WO | WO 00/69406 | 11/2000 |
| JP | 9176033 A | 7/1997 | | WO | WO 00/69407 | 11/2000 |
| JP | 10-046196 A | 2/1998 | | WO | WO 00/69408 | 11/2000 |
| JP | 10-139654 A | 5/1998 | | WO | WO 00/74699 A | 12/2000 |
| JP | 10120542 A | 5/1998 | | WO | WO 00/76458 A2 | 12/2000 |
| JP | 10120542 H | 5/1998 | | WO | WO 01/29163 A | 4/2001 |
| JP | 10139639 A | 5/1998 | | WO | WO 01/34099 A1 | 5/2001 |
| JP | 10139654 A | 5/1998 | | WO | WO 01/34909 A1 | 5/2001 |
| JP | 10-175815 A | 6/1998 | | WO | WO 01/35920 A1 | 5/2001 |
| JP | 410226642 A | 8/1998 | | WO | WO 02/ 07697 A | 1/2002 |
| JP | 11322548 A | 11/1999 | | WO | WO 02/ 07697 A1 | 1/2002 |
| JP | 11346695 A | 12/1999 | | WO | WO 02/064104 A | 8/2002 |
| JP | 200191459 A | 7/2000 | | WO | WO 02/067988 A2 | 9/2002 |
| JP | 2000-351720 A | 12/2000 | | WO | WO 02/074280 A | 9/2002 |
| JP | 2000 302678 | 10/2001 | | WO | WO 03/032941 A | 4/2003 |
| JP | 2001-271096 A | 10/2001 | | | | |
| JP | 2004-000019 A | 1/2004 | | | | |

| | | | |
|---|---|---|---|
| WO | WO 03/039502 A | 5/2003 | |
| WO | WO 2004/022024 A | 3/2004 | |
| WO | WO 2005/097216 A | 10/2005 | |

OTHER PUBLICATIONS

Ebling, FJ, et al., Hair, Journal of Investigative Dermatology, 67:1, 98-105, Jul. 1976.

Ebling. F.J.G. et al., Hair Follicles and Associated Glands as Androgen Targets, Clinics in Endrocrinology and Metabolism 15:2, 319-39, May 1986.

Thornton MJ, et al., Effect of Androgens on the Growth of Cultured Human Dermal Papilla Cells Derived From Beard and Scalp Hair Follicles, Journal of Investigative Dermatology, 97:2, 345-8, Aug. 1991.

Keeton & Gould, eds. Biological Sciences, 4th ed., Chapter 3, p. 66-67 (1986).

Doolittle, The Molecules of Life, Scientific American, p. 38-47 (1985).

Porn-ngarm Limtrakul et al., "Suppressive Effect Of Soybean Milk Protein On Experimentally Induced Tumor In Mice", *Life Sciences*, vol. 53 pp. 1591-1596 (1993).

"Flavosterone S (Soybean Extract Contained Iso-Flavone)", *Ichimaru Pharcos Co., Ltd.*, Published on Dec. 22, 1998.

"A Combined Soybean Crushing-Deordorizing System that Yields 100-200 Mesh Powder for Food Additive Use has been Developed by Shinyu Zoki Co. Ltd. and Mitsubishi Rayon Engineering Ltd.", *Tech Times*, pp. 10 (1978).

"Soy Protein Prevents Skin Tumors From Developing in Mice", *Gene Therapy Weekly*, ISSN 1078-2842, pp. 21 (Nov. 8, 2001).

"Soy Therapy", www.wiseessentials.com/soytherapy.html (email from Jue-Chen Liu, Ph.D. to Cunero et al dated Apr. 13, 2000) Wise Essentials.

Babiarz-Magee et al, "The Expression and Activation of Protease-Activated Receptor-2 Correlate with Skin Color", *Pigment Cell Res*, vol. 17 (2004) pp. 241-251.

Badash et al, "Effect of Gamma Irradiation of Field and Storage Fungi of Wheat, Maize and Soybean", *Chemie Mikrobiologie Technologie der Lebensmittel* (1992).

Blackheart et al, "Ligand Cross-Reactivity Within the Protease-Activated Receptor Family", *The Journal of Biological Chemistry*, vol. 271, No. 28. pp. 16466-16471 (1996).

Galvez et al. "Chemopreventive Property of a Soybean Peptide (Lunasin) That Binds to Deacetylated Histones and Inhibits Acetylation", *Cancer Research*, vol. 61, No. 20, pp. 7473-7478 (Oct. 15, 2001).

Hafez et al, "Effects of Gamma Irradiation on Proteins and Fatty Acids of Soybean", *Journal of Food Science*, vol. 50 (1985) pp. 1271-1274.

Hattori et al, "Effects of sup.60 Co- gamma-rays on Defatted Soybean Powder", *Food Irradiation*, vol. 3, No. 1, pp. 104-110 (1968).

Hermanns et al, "Unraveling the Patterns of Subclinical Pheomelanin-Enriched Facial Hyperpigmentation: Effect of Depigmenting Agents", *Dermatology*, vol. 201 (2000) pp. 118-122.

Hollenberg et al, "Proteinase-Activated Receptor-2 in Rat Aorta: Structural Requirements for Agonist Activity of Receptor-Activating Peptides", *Molecular Pharmacology*, vol. 49, pp. 229-233 (1996).

Jingtian et al, "Studies of Soy Sauce Sterlization and its Special Flavour Improvement by Gamma-Ray Irradiation", *Radiation Physics and Chemistry*, vol. 31, Nos. 1-3, pp. 209-213 (1988).

Kennedy et al, "Prevention of Carcinogenesis by Protease Inhibitors", *Cancer Research*, vol. 54, No. 7 (Suppl), pp. 1999s-2005s (Apr. 1, 1994).

Kennedy, "The Evidence for Soybean Products as Cancer Preventive Agents", *The Journal of Nutrition*, vol. 125, No. 3 Suppl, pp. 733s-743s (Mar. 1995).

Kovacs et al, "Effect of Irradiation and Dielectric Heating on Soybean Ultrastructure, Trypsin Inhibitor, and Lipoxygenase Activities", *Food Structure*, vol. 10, pp. 217-227 (1991).

Lam et al, "Combined Effect of Irradiation and Dielectric Heating on Chemical Properties of Soybeans", *7th Symp. On Radiation Chemistry*, pp. 477-483 (1990).

Liu et al, "Application of Soy in Skin Care", *Journal Nutr.*, vol. 132 (2002) pp. 574S.

Merck Index (12th Edition), Edited by Susan Budavari (1996) Thrombin., entry 9525, p. 1601.

Merck Index (12th Edition), Edited by Susan Budavari (1996) Trypsin, entry 9926, p. 1669.

Mysliborski et al, "Therapy for Acne Vulgaris", *Comprehensive Therapy*, vol. 7, No. 1, pp. 13-16 (Jan. 1981).

Odani et. al, "Studies on Soybean Trypsin Inhibitors. XIII. Preparation and Characterization of Active Fragments from Bowman-Birk Proteinase Inhibitor", *Journal Biochem.*, vol. 83, No. 3, pp. 747-753 (1978).

Paine et al, "An Alternative Approach to Depigmentation by Soybean Extracts via Inhibition of the PAR-2 Pathway", *Journal Investigative Dermatology*, vol. 116 (2001) pp. 587-595.

Scott et al, "Protease-Activated Receptor 2, a Receptor Involved in Melanosome Transfer, is Upregulated in Human Skin by Ultraviolet Irradiation", *Journal Investigative Dermatology*, vol. 117 (2001) pp. 1412-1420.

Scott et al, "Proteinase-Activated Receptor-2 Stimulates Prostaglandin Production in Keratinocytes: Analysis of Prostaglandin Receptors on Human Melanocytes and Effects of PGE2 and PGF2α on Melanocyte Dendricity", *Journal Investigative Dermatology*, vol. 122 (2004) pp. 1214-1224.

Scott et al, "The Proteinase-Activated Receptor-2 Mediates Phagocytosis in a Pho-Dependent Manner in Human Keratinocytes", *Journal Investigative Dermatology*, vol. 121 (2003) pp. 529-541.

Seiberg et al, "Inhibition of Melanosome Transfer Results in Skin Lightening", *Journal Investigative Dermatology*, vol. 115 (2000) pp. 162-167.

Seiberg et al, "Soy Extracts Reduce Hair Growth and Hair Follicle Dimensions", *Hair Science and Technology*, D. Van Neste (editor) (2003) pp. 391-400.

Seiberg et al, "Soymilk Reduces Hair Growth and Hair Follicle Dimensions", *Experimental Dermatology*, vol. 10 (2001) pp. 405-423.

Seiberg et al, "The Protease-Activated Receptor 2 Regulates Pigmentation via Keratinocyte-Melanocyte Interactions", *Experimental Cell Research*, vol. 254 (2000) pp. 25-32.

Seiberg et al, "The Protease-Activated Receptor-2 Regulates Pigmentation via Melanosome Phagocytosis", *Mechanisms of Suntanning*, J. P. Ortonne and R. Ballotti (editors) (2002) pp. 215-278.

Seiberg et al, "The Regulation of Pigmentation by Serine Proteases and Their Inhibitors", Inhibition of Human Proteases: From Target Identification to Therapy, CHI Press (1998) pp. 1-3.

Seiberg, "Keratinocyte-Melanocyte Interactions During Melanosome Transfer", *Pigment Cell Res.*, vol. 14 (2001) pp. 236-242.

Sessa et al, "Toasted Soybean Flour Components with Trypsin Inhibitor Activity", *JAOCS*, vol. 63, No. 6, pp. 784-788 (Jun. 1986).

Sharlow et al, "The Protease-Activated Receptor-2 Upregulates Keratinocyte Phagocytosis", *Journal of Cell Science*, vol. 113 (2000) pp. 3093-3101.

Song et al, "PS04.01.44 Crystal Structure of the Complex of Porcine Pancreatic Trypsin with Kunitz-Type Soybean Trypsin Inhibitor", Crystallography of Biological Macromolecules, p. C-106, XVII Congress and General Assembly of the International Union of Crystallog, (1996) (www.bmsc.wahing...ts/abstracts/S0081.html).

Tan-Wilson, "Relevance of Multiple Soybean Trypsin Inhibitor Forms to Nutritional Quality", *Nutritional and Toxicological Significance of Enzyme Inhibitors in Foods*, Edited by Mendel Friedman, Chapter 22, pp. 391-411 (1985), Department of Biological Sciences, State University of New York at Binghamton.

Van Den Broeke et al, "Topically Applied N-acetylcysteine as a Protector Against UVB-Induced Systemic Immunosuppression", *Journal of Photochemistry and Photobiology, B: Biology*, vol. 27, pp. 61-65 (1995).

Wang et al, "Effects of Soybean Trypsin Inhibitor on Digestive Physiology and Growth and Development of Helicoverpa Armigera Larvae", *Acta Entomologica Sinica*, vol. 38, No. 3 (Aug. 1995) pp. 272-274.

Wenninger et al (Editors), International Cosmetic Ingredient Dictionary and Handbook, Seventh Edition, vol. 2 (1997) pp. 1626, 1654-

1661, 1693-1697, published by The Cosmetic, Toiletry, and Fragrance Association, Washington DC.

Wilson et al, "Immunocytochemical Study of the Interaction of Soybean Trypsin Inhibitor with Rat Intestinal Mucosa", *Gut*, vol. 19 (1978) pp. 260-266.

U.S. Appl. No. 10/611,100, filed Jul. 1, 2003, Halas et al.
U.S. Appl. No. 09/110,409, filed Jul. 6, 1998, Seiberg et al.
U.S. Appl. No. 10/659,598, filed Sep. 10, 2003, Seiberg et al.
U.S. Appl. No. 09/206,249, filed Dec. 7, 1998, Seiberg et al.
U.S. Appl. No. 09/677,511, filed Sep. 29, 2000, Liu et al.
U.S. Appl. No. 09/698,454, filed Oct. 27, 2000, Seiberg et al.

Ogawa, "Current Problem of Research on Hair Growth Mechanisms and Hair Growth Promoters", Fragrance Journal, vol. 5, pp. 1-5 (1989).

Uniqema: "Pharmaceutical and Cosmetic Uses of Diolic Acids", *Research Disclosure*, Kenneth Mason Publications, Hampshire, GB, vol. 444, No. 77 (Apr. 2001).

Huang et al: "Inhibitory Effect of Topical Applications of Nondenatured Soymilk on the Formation and Growth of UVB-Induced Skin Tumors", *Oncology Research*, vol. 14 (2004) pp. 387-397.

http://familydoctor.org/online/famdocen/home/common/cancer/risk/159.html.

Pentapharm, Product "ELHIBIN®" product catalog (1998), Jul. 3, 1998.

Wenninger, et al, International Cosmetic Ingredient Dictionary and Handbook, $7^{th}$ edition, vol. 2 (1997), "Soybean (Glycine Soja) Protein", p. 1332-1333.

McGuire, "Activation of Epidermal Tyrosinase", *Biochemical and Biophysical Research Communications*, vol. 40, No. 5 (1970) pp. 1084-1089.

Kwok et al. "Optimizing Conditions for Thermal Processes of Soy Milk", 50 Journal of Agricultural and Food Chemistry, pp. 4834-4838, (2002), English Abstract.

Van Der Ven et al. Inactivation of Soybean Trypsin Inhibitors and Lipoxygenase by High-Pressure Processing, 53 Journal of Agricultural and Food Chemistry, pp. 1087-1092 (2005), English Abstract.

Adhesion Molecule Expression in Normal Skin and Melanocytic Lesions. Tronnier, Michael, et al. Journal of Cutaneous Pathology, 1997, vol. 24, pp. 278-285.

Altered Cell Signaling and Mononuclear Phagocyte Deactivation During Interacellular Infection. Reiner, Neil E. Immunology Today. 1994, vol. 15, No. 8. pp. 374-381.

A Growth-regulated Protease Activity That is Inhibited by the Anticarcinogenic Bowen-Birk Protease Inhibitor, Paul Billings et al., Proc. Natl. Acad. Sci. 89:3120-3124 (1992).

Amino Acid Sequence and Secondary Structural Analysis of the Corn Inhibitor of Trypsin and Activated Hageman Factor, Walter C. Mahoney:: Journal of Biological Chemistry, vol. 259, No. 13 Jul. 10, 1984, pp. 8412-8416.

Amino Acid Sequences of Double-headed Proteinase Inhibitors from the Seeds of *Canavalia lineata*, Shigeyuki Terada, et al.: Biosci. Biotech. Biochem. vol. 58, (2) pp. 376-379 (1994).

A Serine Protease From Suspension-Cultured soybean Cells, Ze-Jian Guo: Phytochemistry, vol. 47, No. 4 (1998) pp. 547-553, Elsevier Science Ltd, Great Britain.

Astrocytes Regulate Microglial Phagocytosis of Senile Plaque Cores of Alzheimer'S Disease. DeWitt, David A., et al. Experimental Neurology, vol. 1'49, pp. 329-340 (1998) Academic Press, Institute of Pathology, 1998 pp. 329-340.

Aqueous Ethanol Extraction of Soybean Trypsin Inhibitors and Characterization of a Calcium-Sensitive Fraction: Keshun Liu, et al., Journal of Food Biochemistry vol. 15 (1991) pp. 159-168.

Small molecule direct thrombin inhibitors, Michael Wiley, et al., CardioVascular & Renal Review Exp. Opin. Patents 1997 vol. 7, No. 11, Ashley Publications, Ltd., 1997, pp. 1265-1282.

Chemistry and Nutritional value of soybean components. In: Soybeans, chemistry, technology and utilization. Liu, K., pp. 32-35 (Aspen publishers, Inc., Gaithersburg, MD, 1999).

Correlation Between Endogenous Glutathione R. M. Tyrrell and M. Pidoux, Photochem. Photobiol. 47:405-412 (1988).

Cosmetics, Science and Technology, 2nd Edition, Sagarin, vol. 1, pp. 32-43 (1972).

Cosmetics, Science and Technology, 2nd Edition, Sagarin, vol. 1, pp. 72-73 (1972).

Common Disorders of Pigmentation. Hacker, Steven M., Postgraduate Medicine. 1996, pp. 177-186.

Cell-Matrix Interactions in the Genesis of Arteriosclerosis and Altheroma (Effect of Aging). Robert, L., et al. Annals New York Academy of Sciences, 1992, pp. 331-341.

"Chemopreventive Agents: Protease Inhibitors," Ann R. Kennedy, Department of Radiation Oncology, University of PA School of Medicine, Philadelphia, PA 19104, USA Pharmacol. Ther. 78(3):167-209, 1998, Copyright 1998 Elsevier Science Inc.

Current Protocols in Cell Biology, Edited by Juan S. Bonifacino et al. Chapter 6: Electrophoresis and Immunoblotting. Copyright 1999 by John Wiley & Sons, Inc.

Defining Food Components as New Nutrients, Suzanne Hendrick, et al.: American Institute of Nutrition (1994) 1789S-1792S.

Depletion of Cutaneous Glutathione By Ultraviolet Radiation Michael. J. Connor, et al., Photochemistry and. Photobiology 46:239-246 (1987).

Differential Regulation of Human Keratinocyte Growth and Differentiation by a Novel Family of Protease-activated Receptors, Claudia Derian; Cell Growth & Differentiation vol. 8, 743-749, Jul. 1997.

Diazepam Inhibits Phagocytosis and Killing Exerted by Polymorphonuclear Cells and Monocytes From Healthy Donors. Abstract. Immunopharmacology and Immunotoxicology (1989) pp. 701-714.

Do Microglial Cells Phagocyte the B/A4-Amyloid Senile Plaque Core of Alzheimer Diesease? Hachimi, K. et al., Academy of Science, Paris. 1994, vol. 317, pp. 445-451.

Effect of Heat Treatments on Trypsin/Chyomotrypsin Inhibitor Activity of Red Gram (*Cajanus cajan* L.), V.H. Mulimani: Plant Foods for Human Nutrition, vol. 46, No. 2, (1994) 103-107Kluwer Academic Publishers, The Netherlands.

Effects of heat treatment and germination on trypsin and chymotrypsin inhibitory activities in sorghum (*Sorghum bicolor* (L.) Moench) seeds, V.H. Mulimani: Plant Foods for Human Nutrition, vol. 44, No. 3 (1993) 221-226.

Evaluation of the Effects of Hair Re-growth Agents on Lengthening the Anagen Phase Period and Blockade of Anagen phase-Catagen phase Transformation, Kazuto, J. Soc. Cosmet. Chem Japan, vol. 31 No. 4(1997):413-419.

Fluorescence Assay to Monitor Phagocytosis by Blood-Clot Derived Polymorphonuclear Leucocytes Study of Patients With Diabetes and Phagocytosis of Different *Staphyloccoccal* Species. Muxclow, C. Elizabeth et al., Cytobies, vol. 65 The Faculty Press, Great Britain 1991, pp. 15-24.

"Evidence for the Presence of a Protease-Activated Receptor Distinct from the Thrombin Receptor in Human Keratinocytes" Rosemary J. Santulli et al. Proceeding of the National Academy of Sciences of USA, vol. 92, Sep. 1995, pp. 9151-9155.

Glutathione, Ascorbate, and Cellular Protection Alton Meister, Cancer Research Supp. vol. 54:1969s-1975s (1994).

"Glucocorticoid Effect on Hair Growth Initiation: A Reconsideration," Stenn, et al., Skin Pharmacol. , 125-134 (1993).

Handbook of Non-Invasive Methods and the Skin, eds. J. Serup & G. Jemec, Chapter 14.3 (1995).

High-Performance Liquid Chromatographic Analysis of Phytoestrogens in Soy Protein Preparations with Ultraviolet Electrochemical and Thermospray Mass spectrometric Detection, K.D. R. Setchell: Journal of Chromatography 386 (1987) Elsevier Science Publishers B.V., pp. 315-323.

Immunologic Aspects of Lung Diseases and Cystic Fibrosis. Greenberger, Paul A. JAMA, Dec. 1997, vol. 218, No. 22, pp. 1924-1930.

Inflammation in Acne Vulgaris. Webster, Guy F., Jefferson Medical College. 1995, pp. 247-253.

"Interactions of Mast Cell Tryptase with Thrombin Receptors and PAR-2" Marina Molino et al. Journal of Biological Chemistry, vol. 272, No. 7, Feb. 14, 1997 pp. 4043-4049.

Isolation and Properties of Anionic Protease Inhibitors from Buckwheat Seeds, [Y.E. Dunaevsky, et al.: Biochemistry and Molecular Biology International, vol. 40, No. 1, (Sep. 1996) 199-208.

Intercellular Adhesion Molecule-1. van de Stope, A., et al. University Hospital Nijmegen, The Netherlands. 1996 pp. 13-33.

Influence of Nonionic Liposomal Composition on Topical Delivery of Peptide Drugs into *Pilosebaceous* Units: An in Vivo Study Using the Hamster Ear Model; Susan M. Niemiec, et al., Pharmaceutical Research, vol. 12, No. 8, 1995 pp. 1184-1188.

"Inhaled Tryptase Causes Bronchoconstriction in Sheep Via Histamine Release" Jussara F. Molinari, et al., Division of Pulmonary Disease, University of Miami at Mount Sinai Medical Center, Miami Beach, Florida and the Arris Pharmaceutical Corporation, South San Francisco, CA, am J Respir Crit Care Med vol. 154 pp. 649-653, 1996.

Inhibition of Serine Proteases of the Blood Coagulation System by Squash Family Protease Inhibitors, Kaeko Hayaski, et al.: J. Biochem. 116, 1013-1018 (1994).

Interaction of Proteases with Legume Seed Inhibitors. Molecular features, Dinah S. deSeidl: Archivos Latinoamericanos de Nutricion, vol. 44 No. 4-S (1994) 21-S-25-S.

Inflammatory and Immune Responses are Impaired in Mice Deficient in Intercellular Adhesion Molecule I. Sligh Jr., James E., et al. Proc. Natl. Acad., Sci. 1993, pp. 8529-8533.

Identification of Potential Activators of Proteinase-Activated Receptor-2. Fox, Mark T., et al. Federation of European Biochemical Societies. 1997. pp. 267-269.

Kunitz-Type Soybean Trypsin Inhibitor Revisited,Song et al., J. Mol. Biol. 275:347-63 (1998).

"Liposomes—A Selective Drug Delivery System for the Topical Route of Administration; Gel Dosage Form", Mezei & Gulasekharam Journal of Pharmaceutics and Pharmacology, vol. 34 (1982), pp. 473-474.

"Liposomes as a Skin Drug Delivery System", Topics in Pharmaceutical Sciences Mezei, M., (D. D. Breimer and P. Speiser, eds.,), Elsevier Science Publishers B. V., New York, N.Y., 1985, pp. 345-358.

Leukocytosis, Monocytosis and Neutrophilla; Hallmarks of Severe Depression. Maes, M., et al. J. Psychiat. Res. 1992, pp. 125-134.

Mammalian tyrosinase: biosynthesis, processing and modulation by melanocyte stimulating hormone. Jimenez, M., Kameyama, K., Maloy, WL, Tomita Y., and Hearing, V. Proc. Natl. Acad. Sci. USA (1988), 85:3830-34.

McCutcheon's Detergents and Emulsifiers, North American Edition, pp. 317-324 (1986).

Macrophage Uptake of Cholesterol-Containing Particles Derived From LDL and Isolated from Atherosclerotic Lesions. Hoff, H. F., et al. European Heart Jouenal, 1990, pp. 105-115.

Mid-Dermal Elastolysis; An Ultrastructural and Biochemical Study. Fimiani, M., et al., Siena University, 1995, pp. 152-157.

Neutrophil and Monocyte Phagocytosis in Depressed Patients. McAdams C., et al. Neuro-Psychopharmacol & Bio. Psychiat, 1998 pp. 971-984.

Nutrition Communique Soy: Just a Hill of Beans? Clare M. Hasler: Journal of women's Health, vol. 7, No. 5 (1998) 519-523.

Periodontal Disease, Diabetes, and Immune Response; A Review of Current Concepts. Grant-Theule, D., Peridontal Abstracts, vol. 44, No. 3, 1996:69-77.

Partial Purification and Characterization of a Novel Soybean Protease Which is Inhibited by Kunitz and Bowman-Birk Trypsin Inhibitors, Shimpei Morita, vol. 119, No. 4, 1996 p. 711-718.

Photocarcinogenesis and Inhibition of Intercellular Adhesion Molecule I Expression in Cells of DNA-Repair-Defective Individuals. Ahrens, C., et al. The National Academy of Sciences 1997, pp. 6837-6841.

Phytoestrogen Content of Processed Soybean Products, P.A. Murphy: Food Technology, vol. 1, 60-64 (1982).

Preservation of Cosmetics, F. Sharpell Chapter 51, p. 887-900, publicly available prior to Feb. 28, 2001.

Potent Thrombin Inhibitors That Probe the S Subsite; Tripeptide Transition State Analogues Based on a Heterocycle Activated Carbonyl Grup. Costanzo, Michael j., et al. J. Med. Chem. 1996, pp. 3039-3043.

Protease-Activated G Protein Coupled Receptors on Human Platelets and Endothelial Cells. Brass, Lawrence F., et al. University of Pennsylvania, 1997, pp. 234-241.

Protease Activated Receptors Start A Family. Couglin, shaun R., University of California, 1994, pp. 9200-9202.

Primary Structure of a Kunitz-Type Trypsin Inhibitor From Enterolobium Contortisiliquum Seeds, I.F.C. Batista: Phytochemistry vol. 41, No. 4, (1996) 1017-1022.

Protection Against UV-Induced Reactivr Intermediate, D. P. T. Steenvoorden, et al., Photochem Photobiol. 67:651-656 (1998).

Photoprotective Effect of Esterified Glutathione Against Ultraviolet B-Induced Sunburn Cell K. Hanada, et al., J. Invest. Dermatol. 108:727-730 (1997).

Protein Proteinase Inhibitors in legume seeds—Overview, Yehudith Birk: Archivos Latinoamericanos de Nutrition, vol. 44, No. 4-S (1994) 26-S-30-S.

Refractory Periodontitis Associated With Abnormal Polymorphonuclear Leukocyte Phagocytosis and Cigarette Smoking. MacFarlane, Gordon, et al. J. Peridontal, Nov. 1992, University of Minneapolis, pp. 908-913.

"Single-Step Method of RNA Isolation by Acid Guanidinium Thiocyanate-Phenol-Chloroform Extraction," Piotr Chomczynski & Nicoletta Sacchi, Analytical Biochemistry 162, 156-159 (1987), Copyright 1987 by Academic Press, Inc.

Soy Intake and Cancer Risk: A Review of the InVitro and InVivo Data, Mark J. Messina: Nutrician and Cancer vol. 21, No. 2, (1994) 113-131.

Specific identification of an authentic tyrosinase clone. Jimenez, M., K., Maloy, WL, and Hearing, V. J. Biol. Chem. (1989) 264:3397-3403.

Subcellular Distribution of Tyrosinase and Tyrosinase-Related Protein-L; Implications for Melanosomal Biogenesis. Orlow, Seth J., et al. The Socieity for Investigative Dermatology, Inc. 1993, ppp. 55-64.

The Complete Amino Acid Sequence of Rice Bran Trypsin Inhibitor: J. Biochem 102, 2970-306 (1987).

The biochemistry and nutrition group:30 years of research in a developing country, Abraham Levy Benshimol: Archivos LatinoAmericanos De Nutrician, vol. 44, No. 4-S, pp. 5-S-9-S (1994).

"The Bowman-Birk Inhibitor", Int. J. Pept. Protein Res. 25:113-131 (1985).

The Bowman Birk Inhibitor from Soybeans As an Anticarcinogenic Agent), Kennedy, Am. J. Clin. Neutr. 68:1406S-1412S (1998).

The Effect of a Drug-delivery System Consisting of Soybean Phosphatidyl Choline and Medium-chain Monoacylglycerol on the Intestinal Permeability of Hexarelin in the Rat, Urban Fagerholm: J. Pharm. Pharmacol (1998) 50: 467-473.

The Role of Proteolytic Enzymes in the Development of Pumonary Emphysema and Periodontal Disease. Travis, J., et al. University of Georgia and Institute of Molecular Biology. 1994, pp. S143-S146.

The Role of Neutrophil Elastase in Chronic Inflammation. Doring, Grd. Department of Genreal Hygience and Environmental Hygiene, 1994, pp. 114-117.

The Use of Endogenous Antioxidants to Improve Photoprotection Steenvoorden et al., Journal of Photochemistry and Photobiology B:Biology 41 (1997) 1-10.

The Use of Thermospray Liquid Chromatography/Tandem Mass spectrometry for the Class Identification and Structural Verification of Phytoestrogens in Soy Protein Preparations, Robert J. Barbuch: Biomedical and Environmental Mass Spectrometry, vol. 18, (1989) 973-977.

Tryptase Inhibitors Block Allergen-induced Airway and Inflammatory Responses in Allergic Sheep, Warne, William R. Moore, and Richard D. Tanaka, Dept. of Molecular Pharmacology, Inflammation Program, Arris Pharmaceutical Corp, Souch San Francisco, CA, and Department of Research, Division of Pulmonary Diseases, University of Miami at Mount Sinai Medical Center, Miami Beach, Florida, Am J Respir Crit Care Med vol. 152. pp. 2076-2083, 1995.

Trypsin Inhibitor Polymorphism: Multigene Family Expression and Posttranslational Modification, Laurence Quillien: Journal of Protein Chemistry, vol. 16, No. 3 (1997) 195-203.

Trypsin Inhibitor Activity in Commercial Soybean Products in Japan, Yuko Miyagi: J. Nutr. Sci. Vitaminol (1997) vol. 43: 575-580.

Two Groups of Protease Inhibitors Functionally Active in Buckwheat Seeds, Yakov Dunaevsky: soba.shinshu-uac.jp/contents/105.html, publicly available prior to Feb. 28, 2001.

Wheat Germ Trypsin Inhiboors. Isolation and Structural Characterization of Single-Headed and Double-Headed Inhibitors of the Bowman-Birk Type: J. Biochem 100, 975-983 (1986).

The Joy of Soy: www.wheat-grass.com/851_oral_liquid.shtml, Wheatgrass Express, Inc. 1996.

"RQ1 RNase-Free DNASE, Promega," Technical Bulletin No. 518, pp. 1-4, Feb. 2000, Promega Corporation, 2800 Woods Hollow Rd, Madison, WI 53711-5399.

"Invitrogen Life Technologies, ThermoScript RNase H-Reverse Transcriptase," 2001, Invitrogen Corporation, www.invitrogen.com/content.cfm.

Leaflet from Ichimaru Pharcos issued Mar. 7, 1997 "Plant Extract Containing Female Hormone-Like Isoflavones".

Thrombin Inhibitors: Relevant Patent Applications as of Jul. 8, 1998 and Oct. 1, 1996.

Concerns Regarding Soybeans: www.rheumatic.org/soy.htm, publicly available prior to Feb. 28, 2001.

Soy Therapy, www.wiseessentials.com/soytherapy.html (Apr. 13, 2000).

Brochure on Lipoxydase Code 411784, Apr. 1999.

Chapter 8: Antithrombotics/Serine Protease; William Ripka and George Vlasuk, Covads International, San Diego, CA, publicly available prior to Feb. 28, 2001.

Helena Rubinstein Whitening with Soybean? HR has launched "Future White" in Japan, publicly available prior to Feb. 28, 2001.

"Isoral" Soybean power makes your skin clear and moist—Brochure, publicly available prior to Feb. 28, 2001.

Elhibin—Brochure, Centerchem, Inc., publicly available prior to Feb. 28, 2001.

Avon's Anew Positivity Trio Targets Menopausal Women, The Rose Sheet, Feb. 28, 2000, p. 8.

Soybean Technology Improves Skin, Allured's Cosmetics & Toiletries Magazine vol. 115, No. 3, Mar. 2000, p. 22.

Nudit—Advertisement, publicly available prior to Feb. 28, 2001.

Anti-regrowth effect of hair, Dec. 22, 1998, pp. 11-13.

"CaspACE Assay System, Colorimetric," Product Improvements, Neural Notes vol. V, Issue 1 1999, p. 13.

Abstracts of requested patent titles 1996.

Abstract for Product for Damaged hair by Bristol-Myers-Squibb, publicly available prior to Feb. 28, 2001.

Gastric Juice for antiaging—Abstracts 1997.

Soybeans for skin pigmentation—Abstracts 1997.

Soybeans for skin whitening—Chemical Abstracts 1997.

Plant extracts for skin whitening—Abstracts, publicly available prior to Feb. 28, 2001.

EnzChek™ Protease Assay Kits Product Information, Revised Mar. 15, 1999; Molecular Probes, Eugene OR.

Yu D.W., et al., Message of nexin 1, a serine protease inhibitor, is accumulated in the follicular papilla during anagen of the hair cycle, J. Cell Sci. 1995 Dec; 108 (PT 12): 3867-74, NYU School of Medicine, NY 10016, USA.

Seiberg, M., Trypsin-induced follicular papilla apoptosis results in delayed hair growth and pigmentation, Dev Dyn Apr. 1997, 208(4):553-64, Skin Research Center, Skillman, NJ 08558, USA.

Xiang M., et al., A study of Nexin 1 of skin and hair follicle during postnatal development period of rat, Zhongguo Yi Xue Ke Xue Yuan Xue Bao Apr. 1998.;20(2):127-32, Southwestem Hopsital, Third Military Medical University, Chongqing 40038.

* cited by examiner

Soymilk affects hair growth
C57Bl/6 mice, induced hair cycle, day 18
Soymilk
Control Soymilk delays hair growth
Day 4 of hair cycle, C57Bl/6 mice, same magnification Soymilk reduces hair follicle size and pigmentation
Day 7 of hair cycle, C57Bl/6 mice, same magnification for each pair of figures Soymilk reduces hair follicle size and hair shaft thickness
Day 18 of the hair cycle, same magnification Control Soymilk Figure 5. Soymilk induces earlier termination of the hair cycle. Day 21 of the hair cycle, same magnification.

Soymilk and soybean derived proteins reduce hair follicle size
C3H mice, day 7 of the hair cycle, same magnification Soymilk and soybean derived proteins reduce hair follicle size C3H mice, day 7 of the hair cycle, same magnification Soymilk reduces hair follicle size and induces earlier catagen C3H mice, normal (non-induced) hair cycle, day 21

The soybean derived serine proteases BBI and STI reduce hair follicle size and pigmentation, Day 8 of the hair cycle, C57Bl/6 mice, same magnification Figure 12: The expression of the Tyrosinase and TRP-1 proteins in soymilk treated skin is shorter and is reduced in quantity Figure 13 Soymilk reduces human hair growth
Human face, shaved daily, treated with soymilk on the right side for four weeks Soymilk effect on human facial hair growth
One male subject, four weeks treatment Dark blue - untreated side of face
Light blue - soymilk treated side Figure 15 Soymilk reduces hair growth in human legs
Human legs, wax depilated, treated on one side for four weeks C57Bl/6 mouse hair, treated for three weeks with soymilk-containing formulations Control | Ess23 | Ess30

Hair shaft color and thickness of C57Bl/6 mice treated for 15 days with soymilk formulations Control     Ess23     Ess30

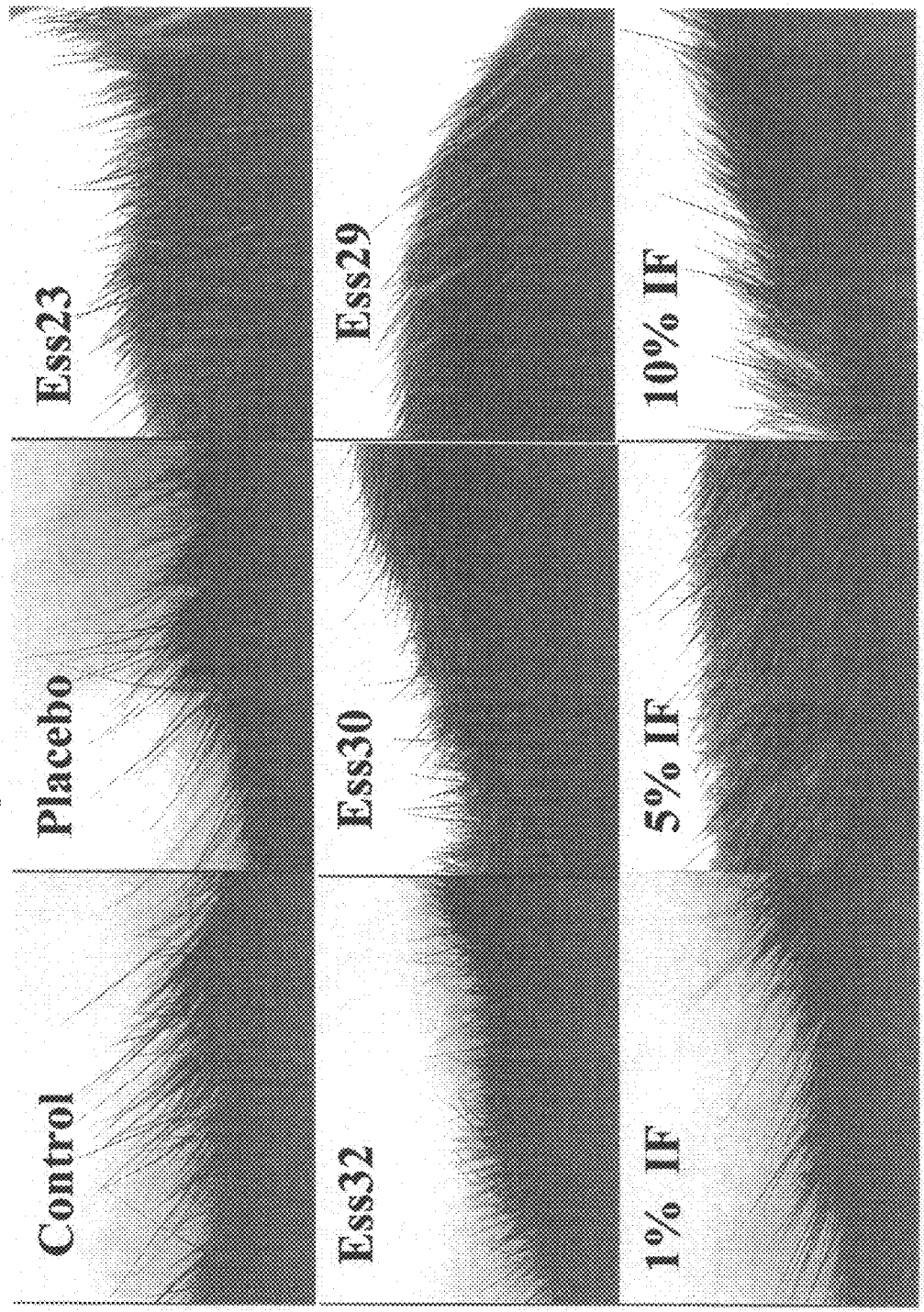
Figure 18  C57Bl/6 mouse hair treated for three weeks with soymilk or isoflavone formulations

REDUCING HAIR GROWTH, HAIR FOLLICLE AND HAIR SHAFT SIZE AND HAIR PIGMENTATION

This application claims the benefit of U.S. Provisional application 60/145,774, filed Jul. 27, 1999.

FIELD OF THE INVENTION

This invention is related to methods and compositions effective for reducing hair growth. More specifically, the present invention is directed to methods for changing the rate of hair growth, reducing the size of the hair follicle and the hair shaft, and reducing hair shaft pigmentation, by topical application of either botanical extracts containing serine protease inhibitory activity and in particular soybean extracts such as soymilk, or mixtures and formulations of the above, combined with other active ingredients such as isoflavones.

BACKGROUND OF THE INVENTION

One main function of mammalian hair is to provide environmental protection. However, that function has largely been lost in humans, in whom hair is kept or removed essentially for social and cosmetic purposes.

Many procedures are used to remove unwanted hair including shaving, electrolysis, plucking, laser and light therapies and injection of therapeutic antiandrogens. These conventional methods are not without their shortcomings. Shaving, for instance, may result in nicks and cuts in the skin's surface, may leave a perception of an increase in the rate of hair regrowth, and may also leave undesirable stubble. While electrolysis may keep an area free of unwanted hair for a prolonged period of time, the process is often expensive and painful and may further result in scarring. Not only may plucking cause pain and discomfort, but it often result in a poor removal of short hair. Several unwanted side effects, such as effects on muscularity, often accompany the use of antiandrogens. For these reasons, better methods for reducing hair growth are needed.

Pseudofolliculitis barbae is an inflammatory hair disorder, most commonly found on the beard area. Inflammatory follicular papules result when hair tips penetrate into the skin rather than passing through the follicular orifice. This process is extremely common in black men because their hairs are frequently curly, exiting the skin at an acute angle. Close shaves, particularly with a razor blade, predispose them to pseudofolliculitis barbae. The most effective treatment available is to allow the hairs to grow well beyond the skin surface. Such a treatment is often not desired.

Hirsutism is a relatively frequent condition affecting about 4% of women. Facial hirsutism often interferes with personal and work activities, and temporary hair removal is a major component in the management of hirsute patients. Shaving is the most frequently used temporary method for facial hair, as plucking, waxing and depilatories are more difficult to tolerate and care must be taken to avoid folliculitis, pigmentation, and scarring. Cosmetic cover-ups are usually used to hide cuts and stubble and electrolysis and thermolysis may be used for permanent hair removal when affordable.

An alternative or complementary desired approach to hair removal, would be a method to reduce hair growth, reduce hair follicle and hair shaft size and reduce hair shaft pigmentation. Such an approach could reduce the visibility of existing hair, making it softer and lighter. When combined with other methods of hair removal such a method could enhance and prolong the removal effect, and reduce the need and frequency of hair removal. Long term use of such an approach could lead to attenuated, soft, pigmentation-reduced hair growth, that is less visible and does not require the use of other removal methods.

Reduced hair growth is desired in the axilla area (fossa axillaris), where deodorants and anti-perspirants are used to control odor trapped within the axillary hairs. It would be desired to have products for under-arm use, which combine deodorant or anti-perspirant activities with reduced hair growth activity.

African type hair is unique in its morphology—a kinky hair shaft with variations in diameter. This complex shaft structure creates the need for specialized grooming products and procedures to ensure that the African type hair maintains cosmetic desired properties.

It is desired to have products that reduce this complexity and make the African type hair more manageable, improving its appearance.

It would be desirable to provide a method for chemically or naturally affecting hair growth, hair follicle and hair shaft size and hair shaft pigmentation, which does not cause unwanted side effects to the user.

SUMMARY OF THE INVENTION

In accordance with the present invention, we have found compositions and methods for affecting changes in mammalian hair growth, hair follicle and hair shaft size and hair pigmentation by topically applying to the skin of a mammal an effective amount of a topically active composition comprising protease inhibitors, botanical extracts, and in particular legume extracts including, but not limited to, soymilk, for a period of time sufficient to affect hair growth, hair follicle and hair shaft size and hair shaft pigmentation. Such topically active compositions may be further combined with other active ingredients including, but not limited to, synthetic or naturally occurring isoflavones, to enhance the desired effects on hair growth and pigmentation.

The compositions and methods of this invention provide a unique, convenient means for delaying hair growth, reducing hair follicle and hair shaft size and hair shaft pigmentation, by using serine protease inhibitors, botanical extracts of the legume family, and in particular, but not limited to, soymilk, containing serine protease inhibitory activity, and their combinations with isoflavones.

BRIEF DESCRIPTION OF THE DRAWINGS

The invention will be more fully understood and further advantages will become apparent when reference is made to the following detailed description of the invention and the accompanying drawings in which:

FIG. 18: Photograph of C57Bl/6 mouse hair after three weeks of treatment with various soymilk and isoflavones formulations.

DETAILED DESCRIPTION OF PREFERRED EMBODIMENTS

Figure 1:
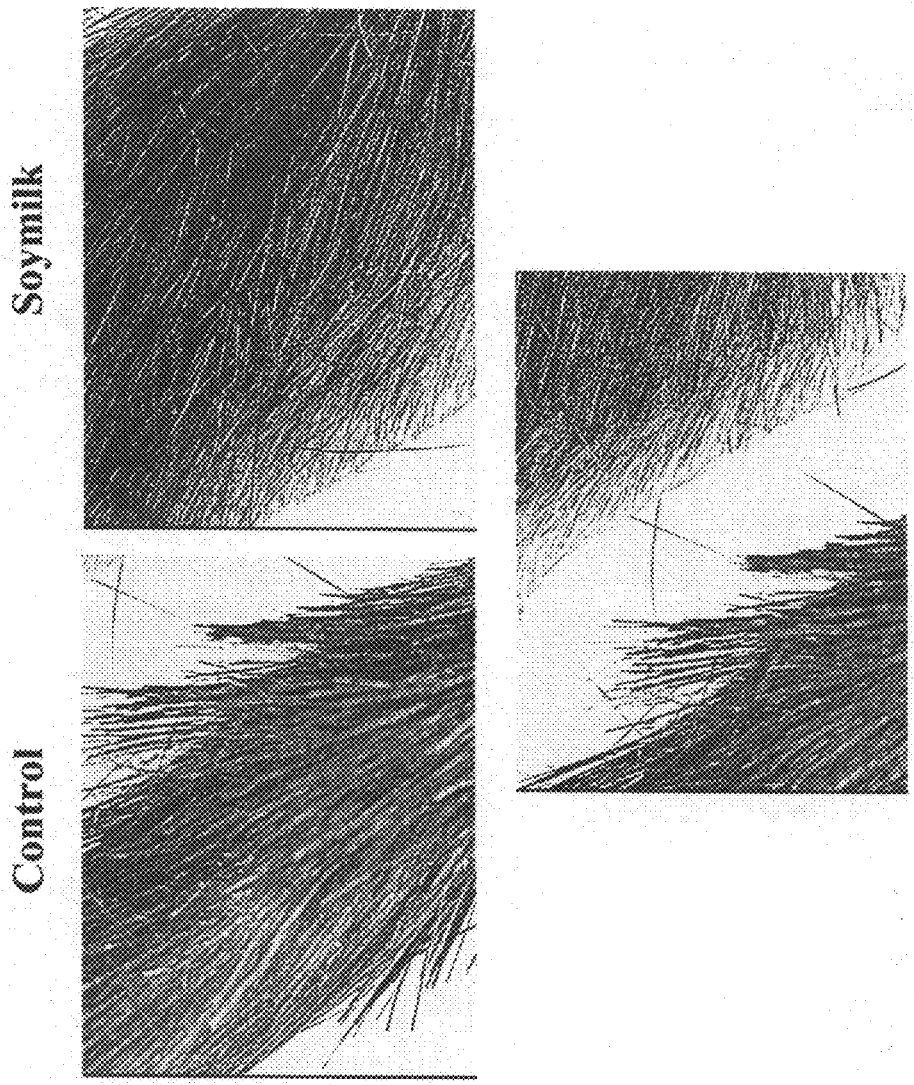
FIG. 1: A photograph of control and soymilk treated C57Bl/6 mouse hair (high magnification).

As used herein, "mammal" shall mean any member "of the higher vertebrate animals comprising the class Mammalia," as defined in Webster's Medical Desk Dictionary 407 (1986), and includes but is not limited to humans. As used herein "(%, w/v)" shall mean grams of a given component per 100 ml of the total composition.

Topically active agents suitable for use in the composition of the present invention include protease inhibitors and natural plant extracts having protease inhibitory activity and mixtures thereof. Preferred protease inhibitors are serine protease inhibitors, and in particular Soybean Trypsin Inhibitor ("STI") and the soybean-derived Bowman Birk Inhibitor ("BBI"). Preferred botanical extracts are of the legume family and in particular bean extracts, such as soymilk. Preferably, the protease inhibitors are present in an amount, based upon the total volume of the composition of the present invention, of from about 0.0001% (w/v) to about 20% (w/v), and more preferably from about 0.001% (w/v) to about 5% (w/v). Preferably, botanical aqueous extracts such as soymilk are present in an amount of 10-99% (v/v), and more preferably from 50-99% (v/v).

This invention also relates to compositions and methods for affecting changes in mammalian hair growth, hair pigmentation and hair shaft and follicle size, comprising topically applying to skin of a mammal an effective amount of a topically active composition comprising one or more compounds derived from one or more of the botanical families leguminosae, solanaceae, gramineae and cucurbitaceae.

We have unexpectedly found that when topically active agents such as described above, and in particular soymilk or soymilk containing formulations, are enriched with isoflavones, and in particular soybean-derived isoflavones, the inhibitory effect on hair growth, hair dimensions and hair pigmentation is enhanced.

Preferably, the isoflavones are present in the botanical aqueous extracts such as soymilk in an amount of 0.000005-15% (v/v), and more preferably from 0.00001-10% (v/v).

If the delivery parameters of the topically active pharmaceutical or cosmetic agent so require, the topically active composition of the present invention may be further comprised of a pharmaceutically or cosmetically acceptable vehicle capable of functioning as a delivery system to enable the penetration of the topically active agent into the hair follicle and the skin.

The pharmaceutical or cosmetic composition may be optionally combined with other ingredients such as moisturizers, cosmetic adjuvants, anti-oxidants, depigmenting agents, anti-aging agents, hair removal agents, hair styling agents, sunscreens surfactants, foaming agents, conditioners, humectants, fragrances, colorants, viscosifiers, buffering agents, preservatives, and the like and mixtures thereof. These will be combined in an amount which will not affect the serine protease inhibitory activity, in order to produce cosmetic or pharmaceutical products such as, non-exclusively, essences, creams, lotions, pastes, gels, powders, patches or injectables and the like for the reduction of hair growth, hair size and hair pigmentation.

The compositions of this invention may be applied prior to, concurrently with or after other active ingredients or compositions to enhance their effect. For example, the compositions of this invention may be applied in conjunction with one or more products whose purpose is to facilitate the removal of hair to actually remove hair, reduce hair visibility, improve hair style or improve hair management. The compositions of this invention may be applied topically prior to, during or following hair removal. They may be applied topically concurrently with one or more of the following group: depilatory agents, shampoo, hair conditioner, styling gel, hair care products, waxing products, shaving products, hair-removal products, after-shave products, deodorant, anti-perspirant, electrolysis, laser hair removal, light-induced hair removal, mask or bath additives.

The compositions of this invention may be applied daily for at least four to eight weeks, by which an effect upon the appearance of hair should be observed. Application may be continued as long as desired to maintain the condition of the hair. Daily application to the face may mitigate the condition of pseudofolliculitis barbae and/or hirsutism; application to the axillary area may reduce hair growth under the arms and application to the scalp and hair may assist in managing and styling African-type hair.

The topically active pharmaceutical or cosmetic composition should be applied in an amount effective to effect changes in mammalian hair growth, hair follicle and hair shaft size and hair shaft pigmentation. As used herein "amount effective" shall mean an amount sufficient to cover the region of skin surface where a delay in hair growth and hair pigmentation and reduced hair size are desired. Preferably, the composition is applied to the skin surface such that, based upon a square cm of skin surface, from about 2 µl/cm$^2$ to about 500 µl/cm$^2$ of topically active agent is present when a delay in hair growth, hair size and hair pigmentation is desired.

We have unexpectedly found that when topically active agents, such as soymilk, or isoflavone-enriched soymilk are topically applied to an animal's skin, a significant delay in hair growth, hair follicle and hair shaft size and hair shaft pigmentation was achieved. We further believe that since the hair growth cycle for humans is often slower than that for mice, it is further likely that the hair growth delay in humans would be considerably longer than in mice.

The invention illustratively disclosed herein suitably might be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Example 1

Depilation of Test Subjects in the Mouse System

C57Bl/6 or C3H mice (male and female) were obtained from Charles River (Kingston, NY), at 8-10 weeks of age and were in the resting (telogen) phase of their respective hair cycle. Hair growth was induced by wax depilation (plucking) of each respective animal's back fur according to the procedure set forth in Stenn, et al., "Glucocorticoid Effect on Hair Growth Initiation: A Reconsideration," 6 Skin Pharmacol., 125-134 (1993). In C57Bl/6 and C3H mice, 8-10 weeks old, the growth phase (anagen) starts synchronously in all hair follicles at the time of depilation. As illustrated in Table 1, the following observations were noticed at the induction site:

TABLE 1

Observations at Induction Site

| Days Post-Induction | Morphological and Histological Observations at the induction site |
|---|---|
| 1-2 (early anagen) | new follicle starts to grow |
| 3 to 4 | hair follicles were fully developed, but the hair shafts were not yet visible |
| 7 to 8 (late anagen) | each mouse had very dark skin; their hair shafts are histologically visible |
| 11-12 | the hair shafts started to penetrate through the epidermis. |
| 14 | each mouse was covered with short hairs |
| 19 | the regression of the follicle (catagen) was observed histologically |
| 21 to 25 | the hair follicle is back to resting phase. |

As shown in Table 1, the hair growth was visible several days after depilation as the pink skin of the animal began to darken. This is likely due to hair pigmentation in the shaft since the C57Bl/6 and C3H mice contained melanocytes only in the hair follicles and not in the dorsal epidermis. Similar hair growth pattern was documented in our international application No. PCT/US 97/11033, when chemical depilation using commercially available products was performed.

Since the murine hair cycle varies not only between strains, but also amongst individual animals, the status of the hair cycle was analyzed in each animal on study. A 2 cm by 1 cm skin sample was isolated from each mouse with scissors, fixed with a 10% buffered formalin solution having a pH of about 6.9-7.1 at 25° C. (Stephens Scientific), and then formed into a paraffin block according to well-known procedures. The block was then microtomed, and sections were stained with H&E or Fontana-Mason stain. Sections were examined histologically in order to verify the phase of the hair cycle, the size of the hair follicle and hair shaft and the level of hair pigmentation, using procedures well known in the art. Hair length was assessed visually, and by using a low magnification (×8) dissecting microscope.

This Example, as well as the one described in our international application No. PCT/US 97/11033, shows that the hair growth cycle for C57Bl/6 and C3H mice averaged about 25 days and reports similar timing of hair follicle and shaft development regardless of the method used for depilation.

Example 2

Preparation of Soymilk and Soymilk Formulations

One way to make soymilk is to soak the soybeans in deionized or purified water for several hours, and grind them after they were fully hydrated, with the addition of small quantities of water. (The grinding process allows the soybean milk to be extracted). After collection, the soybean milk may be filtered to remove any residual parts of the bean husk. The soymilk used in the formulations described below can be fresh soymilk as described above, or may be made from soybean powder and water. The soybean powder is milled from soybeans and may also be lyophilized, spray dried, or freeze-dried and the resulting soymilk may or may not be filtered. Such prepared soymilk may have from about 1 to about 90% by weight dry soybean powder. Another example is the use of soymilk powder, made from lyophilized, spray dried or freeze-dried soymilk, with the addition of water and finished with or without filtration or homogenization. Other methods of soybean extraction could also be used to create the active ingredients in the formulations described below. For example, the active ingredients could be extracted from ground soybeans using ethanol/water mixtures, followed by the removal of the ethanol from the extract, in such ways that the serine protease inhibitory activity of the soybean will be retained, and preferably that the protein STI will remain intact.

The soy products useful in this invention may be produced from all soybean species, regardless of their geographic origin, sun exposure, harvest time and the like. However, specific strains, geographic origins or growth conditions might be preferred. For example, but not limiting to, soybean strains particularly rich in its Soybean Trypsin Inhibitor (STI) content or in isoflavone content, or growth conditions that result in STI or isoflavone enrichment in the bean, might be preferred. It should be noted that the soy products useful in the compositions of this invention have a distinctive odor, which may be tolerable in some cultures, but is undesired in others. If necessary, the odor of the compositions of this invention may be reduced by using soybean products derived from specific strains of soybeans known to produce reduced-odor, including, but not limited to, lipoxygenase-2-deficient beans and those having modified sugar profile, and the like. A process to reduce oxygen levels in the formulation may also reduce the odor. Various masking agents or fragrances may also be used to mask the odor.

The compositions of this invention may further comprise surfactants, moisturizers, humectants, conditioners, fragrances, colorants, preservatives, anti-oxidants, depigmenting agents, hair removal agents, anti-aging agents, sunscreens, foaming agents, cosmetic adjuvants, buffering agents or mixtures thereof.

The compositions of this invention may be left on the skin for a period sufficient to effect changes. For example, the compositions of this invention may be applied to the skin daily treatment for at least about four weeks, more preferably, the composition should applied daily for at least eight weeks.

Another method according to this invention is a method to reduce or prevent pseudofolliculitis barbae. Daily application of the compositions of this invention may reduce or prevent this condition. The compositions of this invention may also be applied daily to the axilliary area to reduce hair growth. Furthermore, the compositions of this invention may be applied daily to the scalp to style and improve management of African type hair.

As shown in our co-pending U.S. patent application Ser. No. 09/110,409, numerous soymilk-based formulations could be used to reduce pigmentation. All these formulations could also be used to reduce hair growth. Some particularly preferred examples of soymilk formulations and soymilk formulations containing isoflavones are shown in table 2 below. An example for an isoflavones preparation that could be used in this invention is Flavosterone SE from Ichimaru, Japan, which contains about 0.1% pure isoflavones. In all these formulations, soymilk could be replaced with the appropriate quantities of soybean powder or soymilk powder and water.

Example 3

Preparation of Topically Active Compositions Containing Soybean Derived Protease Inhibitors Soybean trypsin inhibitor (STI) and Bowman-Birk inhibitor (BBI), from Sigma-Aldrich Corporation were mixed into a 0.1M phosphate buffered saline (PBS, Gibco-BRL, Gaithersburg, MA), pH 7.4, in concentrations of 1% to 0.001% (w/v). Four volumes of the resulting solutions were then mixed with 1 volume of (100 mg/ml) liposomes vehicle, which was prepared by the methods described in Niemiec et. al, in order to yield the topically active composition. Nonionic liposomes preparations, such as those disclosed in Niemiec et al., "Influence of Nonionic Liposomal Composition On Topical Delivery of Peptide Drugs Into Pilosebaceous Units: An In Vivo Study Using the Hamster Ear Model," 12 Pharm. Res. 1184-88 (1995) ("Niemiec"), which is incorporated by reference herein in its entirety, are well known in the art, and are described our U.S. patent application Ser. No. 09/110,409. GDL liposomes were prepared as set forth in Niemiec, et al., above, with the exception of the following changes: the non-ionic liposomal formulation contained glycerol dilaurate (Emulsynt GDL, ISP Van Dyk)/cholesterol (Croda)/polyoxyethylene-10-stearyl ether (Brij76, ICI)/polyoxyethylene-9-lauryl ether, as at ratio of 37.5:12.5:33.3:

TABLE 2

Soymilk Essence formulations: Soybean Essences

| | 1 | 6 | 8 | 21 | 22 | 23 | 24 | 25 | 26 |
|---|---|---|---|---|---|---|---|---|---|
| Soymilk | 87.42% | 89.04% | 96.09% | 96.05% | 96.05% | 95.70% | 94.40% | 94.40% | 92.40% |
| Phenoxyethanol | 0.73% | | | | | | | | |
| Phenoxyethanol and Parabens | | 1.00% | 1.00% | 1.00% | 1.00% | 1.00% | 1.00% | 1.00% | 1.00% |
| Glycerin | 2.50% | 2.50% | | | | | | | |
| Cyclomethicone | 2.00% | | | | | | | | |
| Aluminum Starch Ocetyl Succinate | 0.75% | | | | | | | | |
| Sucrose Cocoate | 1.00% | 1.00% | | | | | | | |
| PEG-6 Capric/Caprylic Triglycerides | 3.00% | 3.00% | | | | | | | |
| Disodium EDTA | 0.10% | 0.10% | | | | 0.05% | 0.05% | 0.05% | 0.05% |
| Polyacrylamide/Laureth-7/$C_{13-14}$ Isoparrafin | 2.50% | 2.75% | 2.90% | 2.90% | 2.90% | 3.20% | 3.50% | 3.50% | 3.50% |
| Ascorbic Acid | | 0.01% | | | | | | | 1.00% |
| Butylated Hydroxytoluene | | 0.10% | 0.01% | 0.05% | 0.05% | 0.05% | 0.05% | 0.05% | 0.05% |
| Polysorbate 20 | | 0.50% | | | | | | | |
| Lactoferrin | | | | | | | 1.00% | 1.00% | 1.00% |
| Tocopherol | | | | | | | | | 1.00% |
| TOTAL | 100.00% | 100.00% | 100% | 100% | 100% | 100% | 100% | 100% | 100% |

| | 27 | 28 | 29 | 30 | 31 | 32 | 33 | 34 | 35 |
|---|---|---|---|---|---|---|---|---|---|
| Soymilk | 90.70% | 94.70% | 85.70% | 90.70% | 93.70% | 94.70% | | | |
| Phenoxyethanol and Parabens | 1.00% | 1.00% | 1.00% | 1.00% | 1.00% | 1.00% | 1.00% | 1.00% | 1.00% |
| Glycerin | 5.00% | | | | | | | | |
| Disodium EDTA | 0.05% | 0.05% | 0.05% | 0.05% | 0.05% | 0.05% | 0.05% | 0.05% | 0.05% |
| Polyacrylamide/Laureth-7/$C_{13-14}$ Isoparrafin | 3.20% | 3.20% | 3.20% | 3.20% | 3.20% | 3.20% | 3.20% | 3.20% | 3.20% |
| Ascorbic Acid | | | | | | | | | |
| Butylated Hydroxytoluene | 0.05% | 0.05% | 0.05% | 0.05% | 0.05% | 0.05% | 0.05% | 0.05% | 0.05% |
| Deionized Water | | | | | | | 90.70% | 90.70% | 85.70% |
| Dow Corning 200 Fluid | | 1.00% | | | | | | | |
| Flavosterone SE | | | 10.00% | 5.00% | 2.00% | 1.00% | | | |
| Soymilk Power | | | | | | | 5.00% | | |
| Soybean Extract using Ethanol/Water Mixture | | | | | | | | 5% | 10% |
| TOTAL | 100% | 100% | 100% | 100% | 100% | 100% | 100% | 100% | 100% |

16.7. Either PBS or Hepes buffer, 0.05M, pH 7.4 (Gibco-BRL of Gaithersburg, Md.) were used as the aqueous phase in the preparation of the liposomes.

Example 4

Soymilk Delays Hair Growth and Reduce Hair Follicle and Hair Shaft Size and Hair Shaft Pigmentation C57Bl/6 mice were induced for a new hair cycle as described in Example 1, and treated daily with soymilk.

ANIMALS were observed daily for their hair growth pattern, and skin biopsies were taken at important time points of the hair cycle. As a result of soymilk treatment the hair growth of the treated mice was delayed, and their hairs were visibly thinner, and smoother to touch. Treated mice did not show skin darkness at days 7-8 of the hair cycle, as expected, and hair shafts were not visible at days 11-12 as in the control animals. In average, the hair cycle of the soymilk treated mice was delayed by 3-6 days. FIG. 1 is a picture of the mice fur, showing the difference in hair appearance, color, size and thickness following soymilk treatment.

Figure 2:
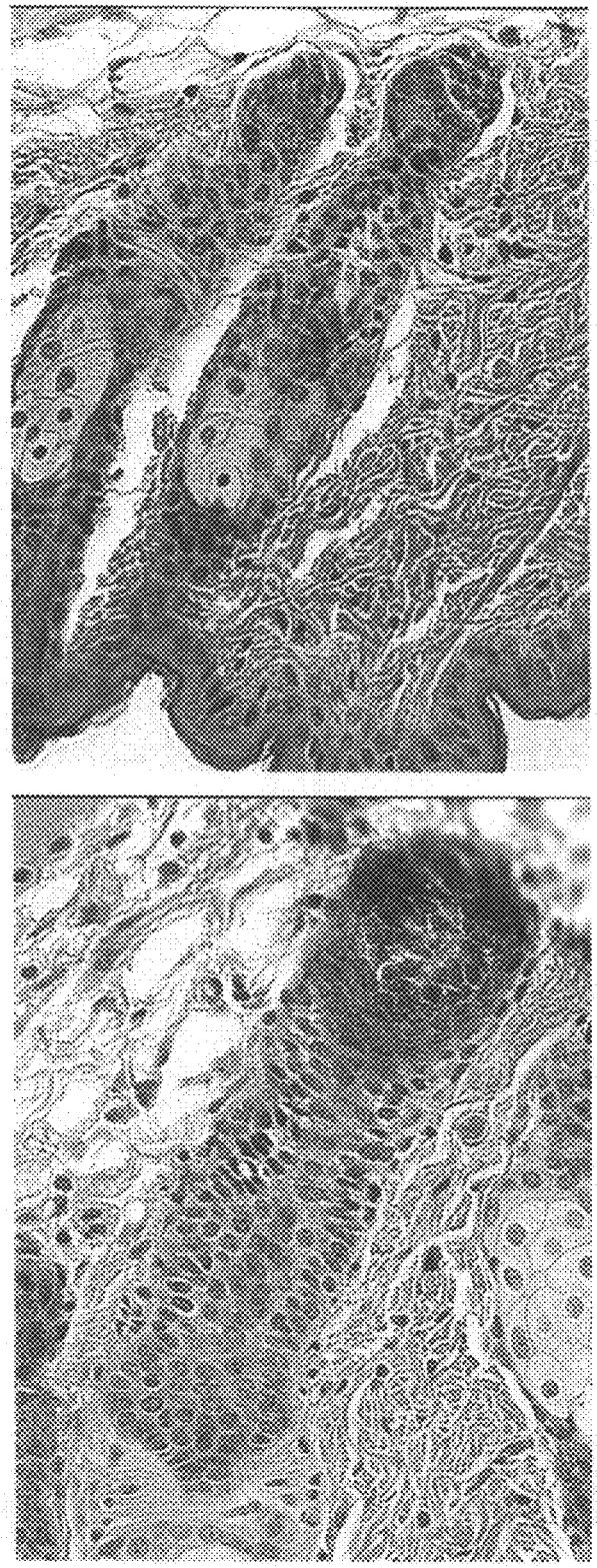
FIG. 2: Histological sections of control and soymilk treated C57Bl/6 mouse hair follicles at day four of the hair cycle.

Histological examination of the biopsied skin samples confirmed these observations. As shown in FIG. 2 by Fontana-Mason (F&M) staining, at day four of the hair cycle the untreated hair follicle is fully developed, as expected, containing all the cellular layers and pigment deposition. In contrast, the soymilk treated sample, (shown at same magnification), shows a smaller and not as fully developed hair follicle, with no pigment deposition.

Figure 3:
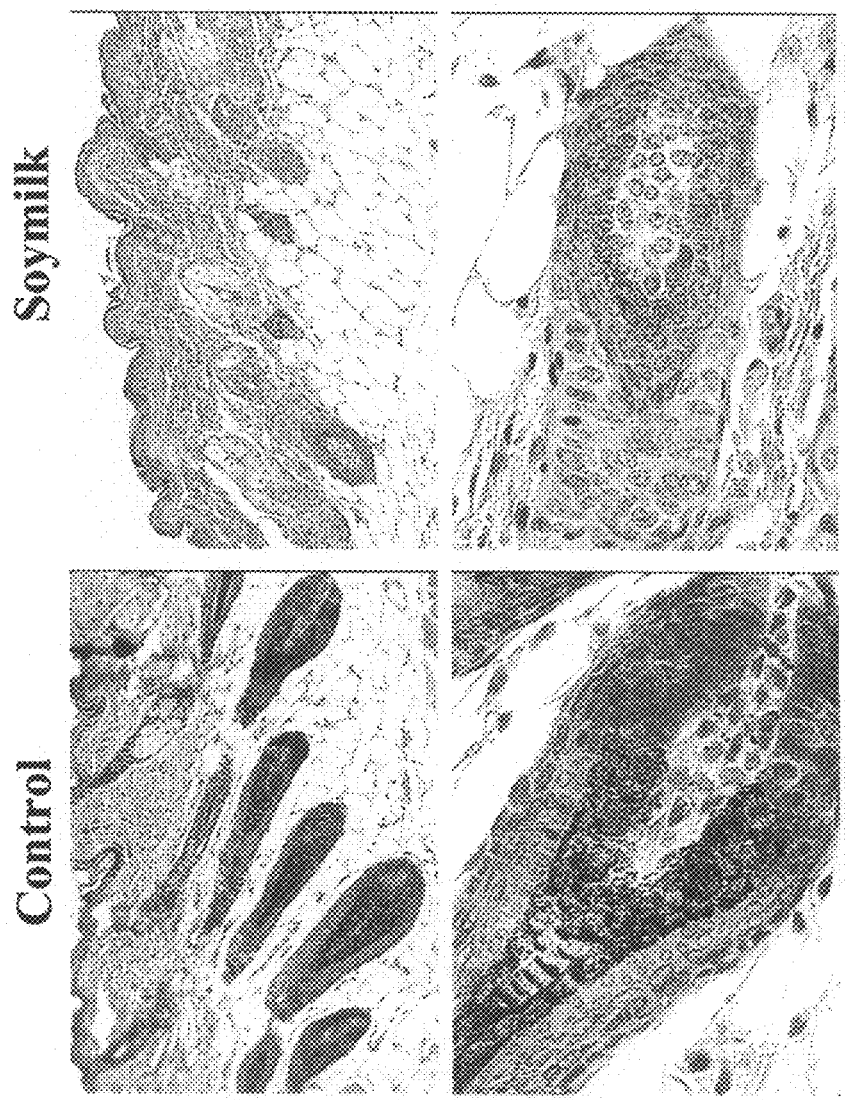
FIG. 3: Histological sections of control and soymilk-treated C57Bl/6 mouse hair follicles at day seven of the hair cycle, high and low magnifications.

FIG. 3 shows two sets of histological sections stained with F&M, of lower and higher magnification. These sections are from day seven of the hair cycle. The upper panel shows that soymilk treated skin has smaller, shorter, and less pigmented hair follicles than the untreated control. The lower panel shows a higher magnification of the follicles, further demonstrating the difference in hair follicle and hair shaft size and pigmentation following soymilk treatment.

Figure 4:
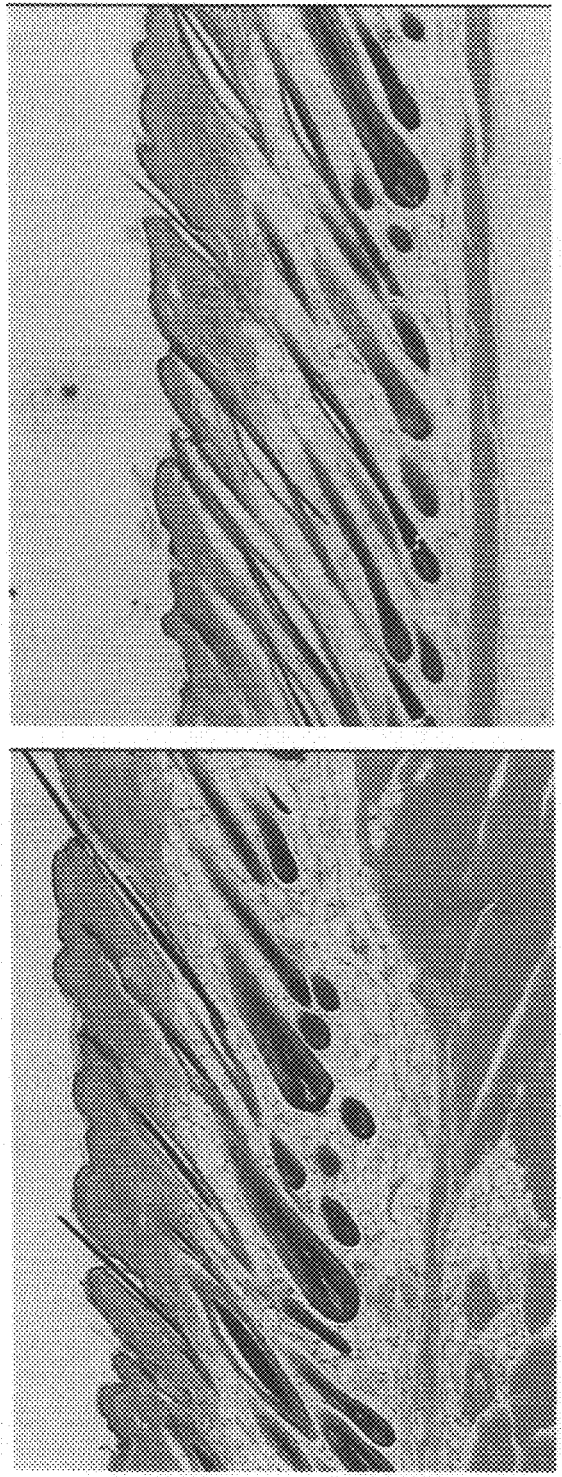
FIG. 4: Histological sections of control and soymilk-treated C57Bl/6 mouse hair follicles at day 18 of the hair cycle.

FIG. 4 shows low magnification of F&M stained skin sections at day 18 of the hair cycle. At this magnification it is obvious that soymilk treatment results in reduced hair follicle size, which leads to reduced hair shaft length and thickness, and reduced total pigment deposition within the treated follicles.

Figure 5:
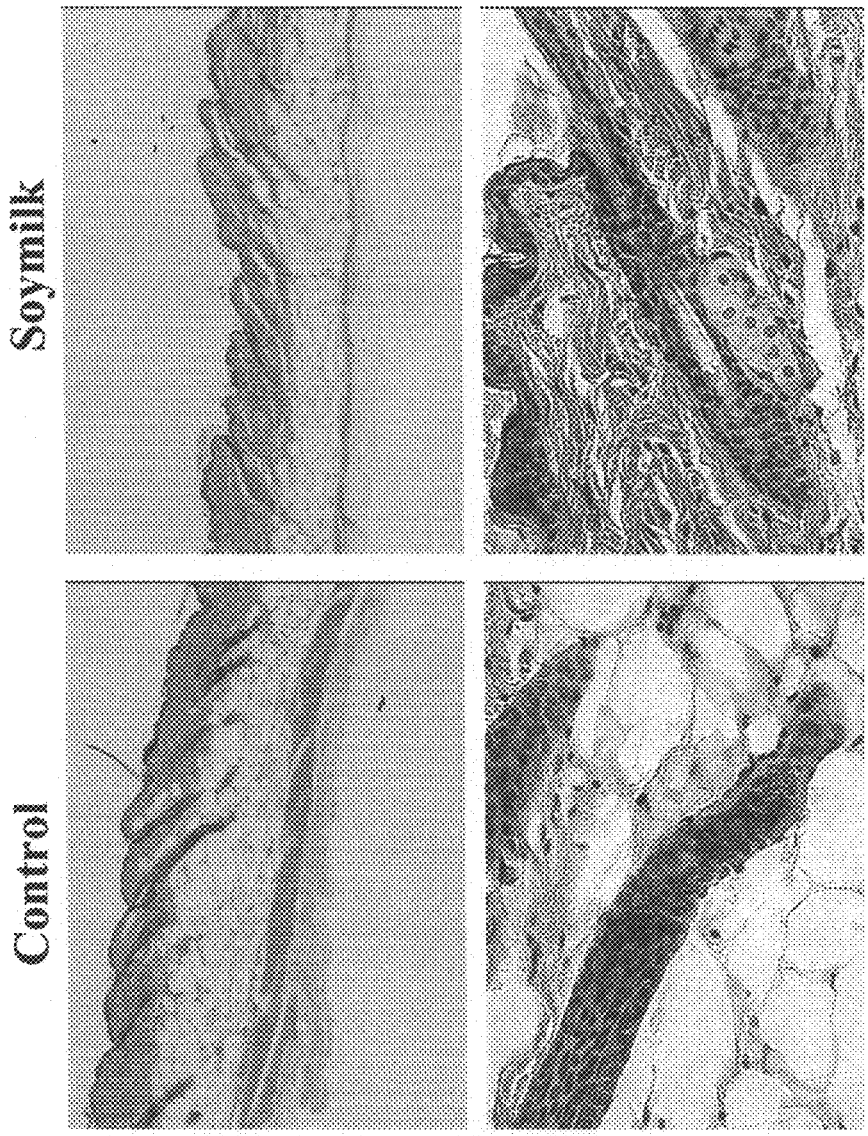
FIG. 5: Histological sections of control and soymilk-treated C57Bl/6 mouse hair follicles at day 21 of the hair cycle.

FIG. 5 shows skin sections at day 21 of the hair cycle, with two magnifications. The upper panel demonstrates that the control animals were in the catagen stage, when hair follicles are regressing. Soymilk treated follicles, on the other hand, had already completed the catagen stage, as they are shown in telogen, the resting stage. This indicates that not only the hair cycle was delayed following soymilk treatment, it was also prematurely terminated. The lower panel demonstrates the catagen control follicle and the shorter, telogen (resting) soymilk-treated follicle using higher magnification.

Example 5

The Effects of Soymilk on Hair Growth, Size and Pigmentation are Reproducible in C3H Mice In order to verify that the effect of soymilk on hair growth is not specific to C57Bl/6 mice, we repeated the experiment described in Example 4 using the brown haired (Agouti) C3H mice. The results of these experiments were similar both visually and histologically. Soymilk delayed hair growth and reduced hair follicle and hair shaft size and pigment deposition in the C3H mice.

Histological analysis confirmed these visual observations. As shown in the upper panel of FIG. 6, using F&M staining, at day seven of the hair cycle soymilk treated follicles are smaller and accumulate less pigment than untreated controls. The upper panel of FIG. 7 (F&M staining) shows a lower magnification of the same skin sections, demonstrating the thinner and less pigmented follicles following soymilk treatment.

Figure 8:
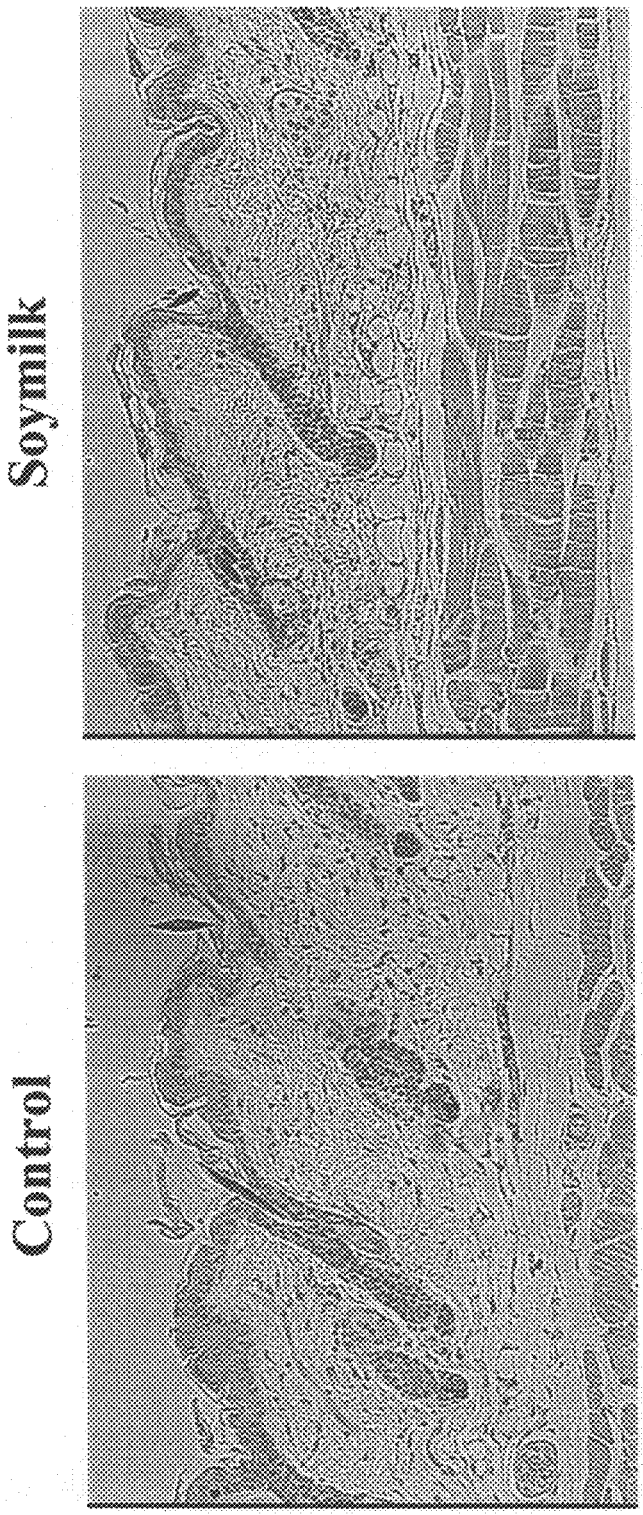
FIG. 8: Histological sections of control and soymilk-treated C3H mouse hair follicles at day 21 of the hair cycle.

FIG. 8 shows F&M stained skin sections at day 21 of the hair cycle. As shown for the C57Bl/6 mice, following soymilk treatment the hair cycle terminates prematurely. Soymilk treated follicles are in the resting state, while untreated control follicles are still in catagen.

Example 6

The Effects of Soymilk and Soybean Derived Serine Protease Inhibitors on Hair Growth, Size and Pigmentation In search for a mechanism to explain the effect of soymilk on hair growth, we tested the effect of the soymilk-derived serine protease inhibitors, STI and BBI.
We had shown earlier that these proteins induce depigmentation in skin, by affecting the PAR-2 pathway (U.S. patent application Ser. No. 09/110,409).

Figure 9:
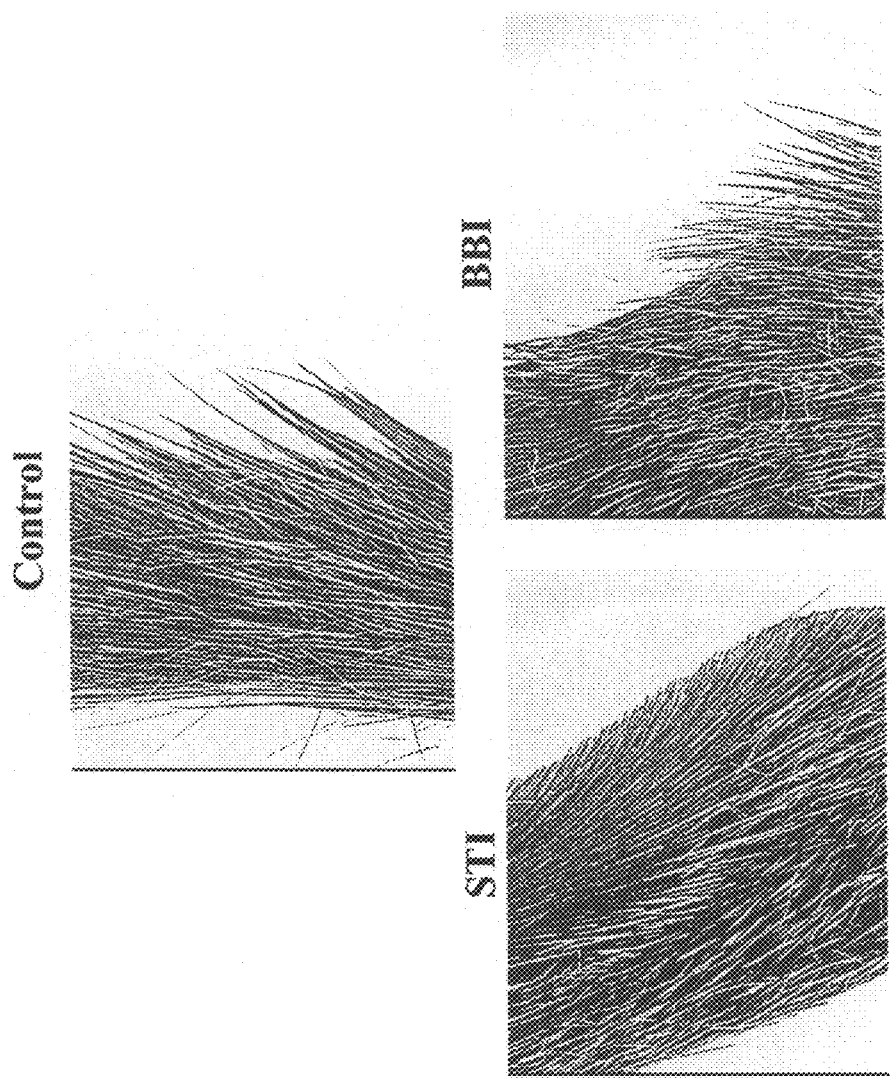
FIG. 9: A photograph of control and soymilk-derived proteins treated C3H mouse hair (high magnification).

The experiments described in Example 4 were repeated using STI, BBI, and soymilk. STI and BBI were used in a PBS-liposome vehicle as described in Example 3. Visual observations throughout the hair cycle confirmed that both STI and BBI could delay hair growth and reduce hair follicle and hair shaft size, similar to soymilk (see hair pictures in FIG. 9). Using high concentrations of STI or BBI, the effect on hair growth and pigmentation was substantial.

Figure 6:
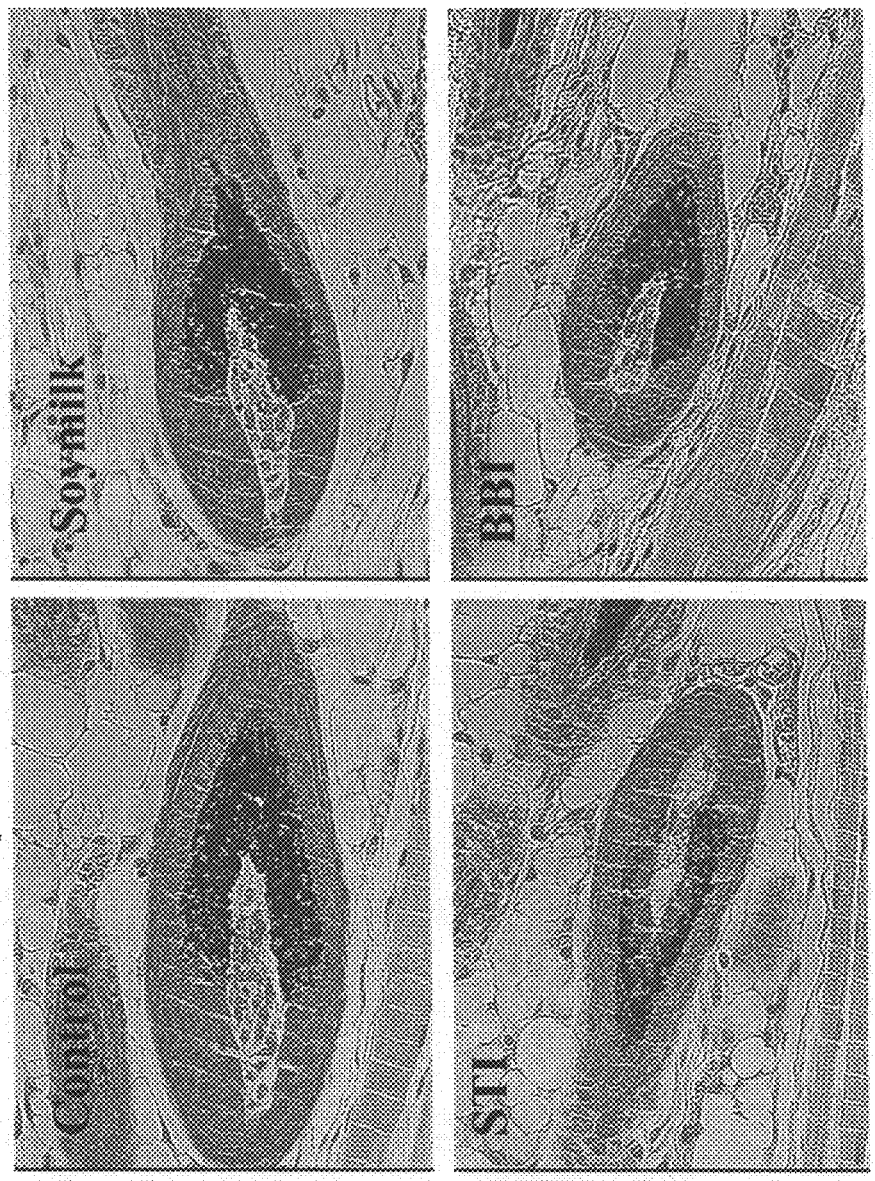
FIG. 6: Histological sections of control, soymilk, and soymilk-derived proteins-treated C3H mouse hair follicles (High magnification) at day seven of the hair cycle.
Figure 7:
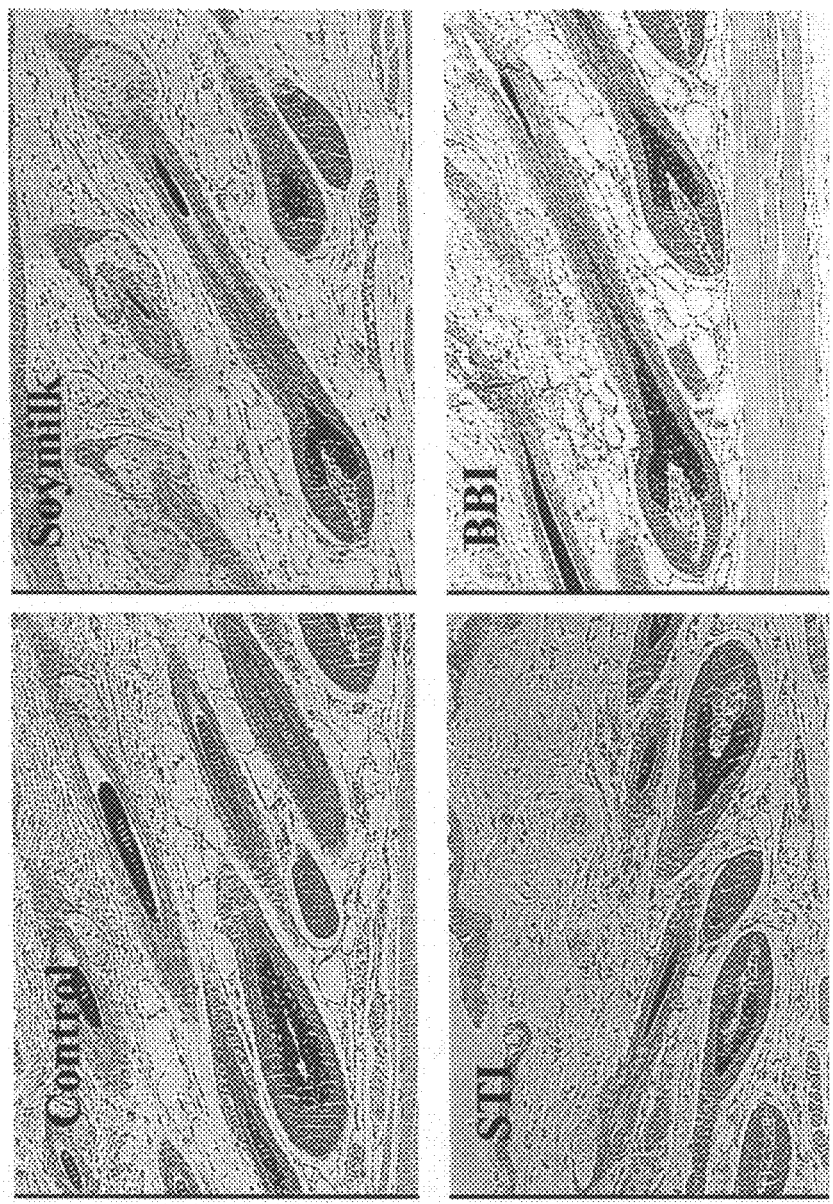
FIG. 7: Histological sections of control, soymilk, and soymilk-derived proteins-treated C3H mouse hair follicles (lower magnifications) at day seven of the hair cycle.
Figure 10:
FIG. 10: Histological sections of control and soymilk-derived proteins-treated C57Bl/6 mouse hair follicles (High magnification) at day eight of the hair cycle.

Histological analysis confirmed these finding. As shown in FIG. 6, at day seven of the hair cycle 1% of STI and 1% of BBI reduce hair follicle and hair shaft size and hair shaft pigmentation in C3H mice. FIG. 7 shows lower magnification sections of the same day into the hair cycle, demonstrating smaller hair follicles and hair shafts and reduced pigmentation, relative to untreated control, with soymilk, STI or BBI treatment. FIG. 10 shows that STI and BBI have the same effect in C57Bl/6 mice too, demonstrating smaller and less pigmented follicles. Taken together, this example shows that STI and BBI are soybean-derived serine protease inhibitors, found in soymilk, that could delay hair growth, reduce hair follicle and hair shaft size and reduce hair pigmentation. STI and BBI could represent a part of the soymilk ingredients that affects hair growth.

Figure 11:
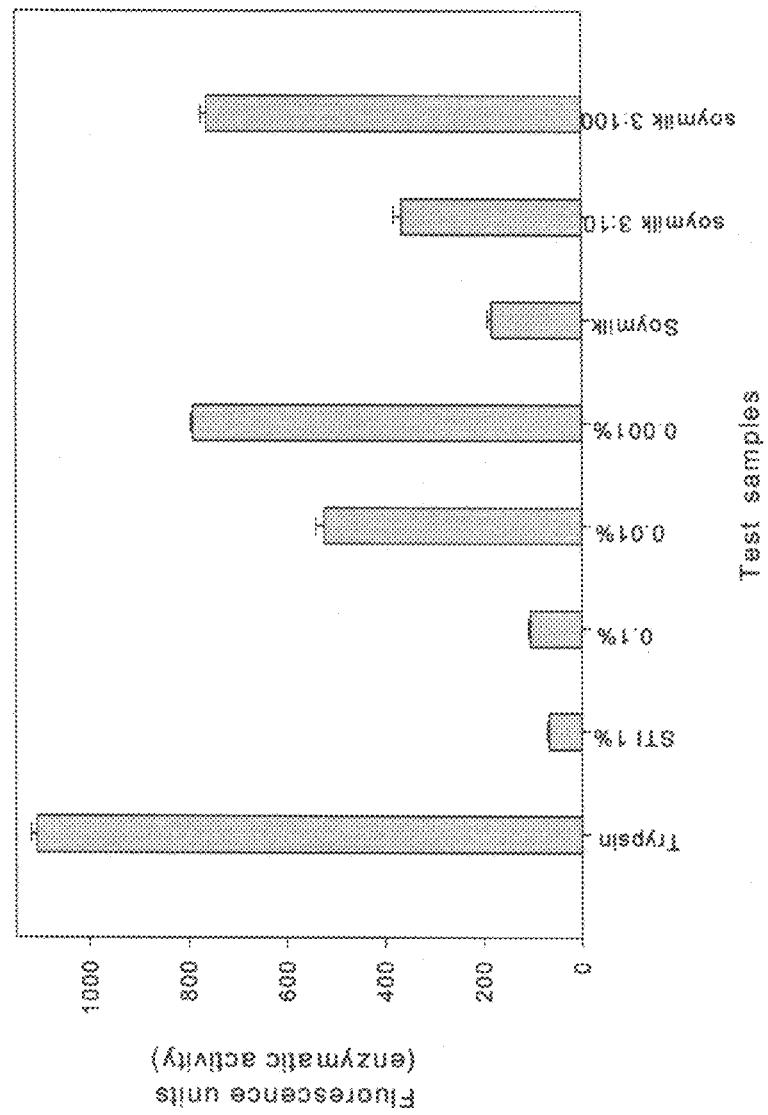
FIG. 11: A graph demonstrating the trypsin inhibitory activity of soymilk.

In order to support the hypothesis that STI and BBI in soymilk are involved in the hair growth effects described above, we tested soymilk for its serine protease inhibitory activity. An enzymatic assay was performed using "Enzchek", a protease digestion fluorescent test system made by Molecular Probes of Eugene, Oreg. Using 100 units of trypsin (from Sigma chemicals, St. Louis Mo.) the test system produced fluorescence reading of about 1100 units. This reaction was inhibited with increasing concentrations of STI, as expected from a known trypsin inhibitor. Serial dilutions of soymilk were tested in this assay, and found to inhibit trypsin activity. As shown in FIG. 11, soymilk exerts trypsin inhibitory activity similar to about 0.2% of pure STI. This suggests that soymilk could exert its hair growth effect, at least in part, by STI and BBI.

Example 7

Soymilk Induces Changes in Tyrosinase and TRP-1 Protein Expression

The histological analyses of soymilk treated skin samples described in the examples above show dramatic reduction in pigment deposition within the hair follicle. To further understand the mechanism of soymilk-induced depigmentation, we studied tyrosinase, the key enzyme in melanogenesis and Tyrosinase-Related Protein-1 (TRP-1), the enzyme that stabilizes tyrosinase. C57Bl/6 and C3H mice were treated as described above, and samples were collected throughout the study for protein analysis. Protein extraction and Western blot analysis were performed using standard procedures, such as the one described in Current Protocols in Cell Biology, Edited by Juan S. Bonifacino et al. Chapter 6: Electrophoresis and Immunoblotting. Copyright 1999 by John Wiley & Sons, Inc., which is incorporated herein by reference in its entirety. An example of one such study is shown in FIG. 12.

Equal amounts of skin-extracted proteins were probed with the anti-tyrosinase antibody "anti PEP1", and with the anti-TRP-1 antibody "anti PEP7" which are described in Jimenez, M., Kameyama, K., Maloy, W L, Tomita Y., and Hearing, V. Mammalian tyrosinase: biosynthesis, processing and modulation by melanocyte stimulating hormone. Proc. Natl. Acad. Sci. USA (1988), 85:3830-34, and Jimenez, M., K., Maloy, WL, and Hearing, V. Specific identification of an authentic tyrosinase clone. J. Biol. Chem. (1989) 264:3397-3403, which are incorporated herein by reference in their entirety.

Figure 12:
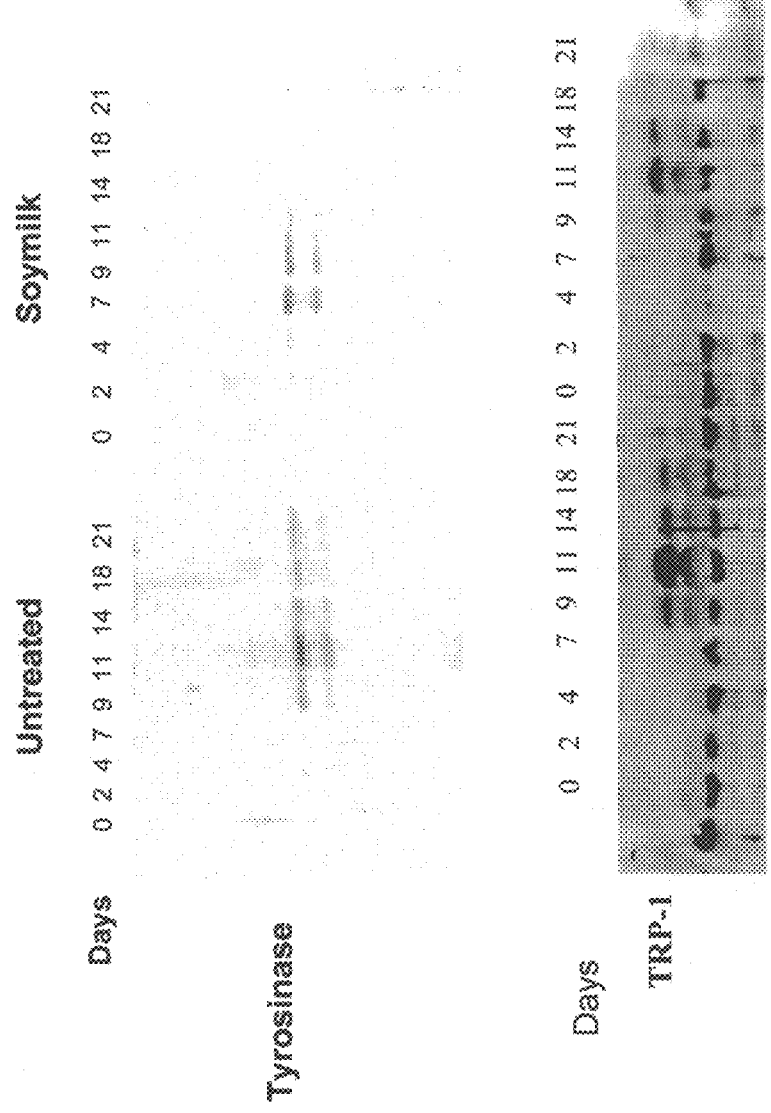
FIG. 12: Western blot of C57Bl/6 mouse skins throughout the hair cycle, demonstrating reduced tyrosinase and TRP-1 protein levels following soymilk treatment.

As shown in FIG. 12, The expression of Tyrosinase and TRP-1 proteins is dramatically affected by soymilk treatment. Tyrosinase and TRP-1 levels are reduced, and the duration of the expression is shortened. These two factors affect overall hair pigmentation, which is reduced due to the reduced level and shorter duration of melanogenesis.

Example 8

Soymilk Reduces Human Facial Hair Length and Thickness

Figure 13:
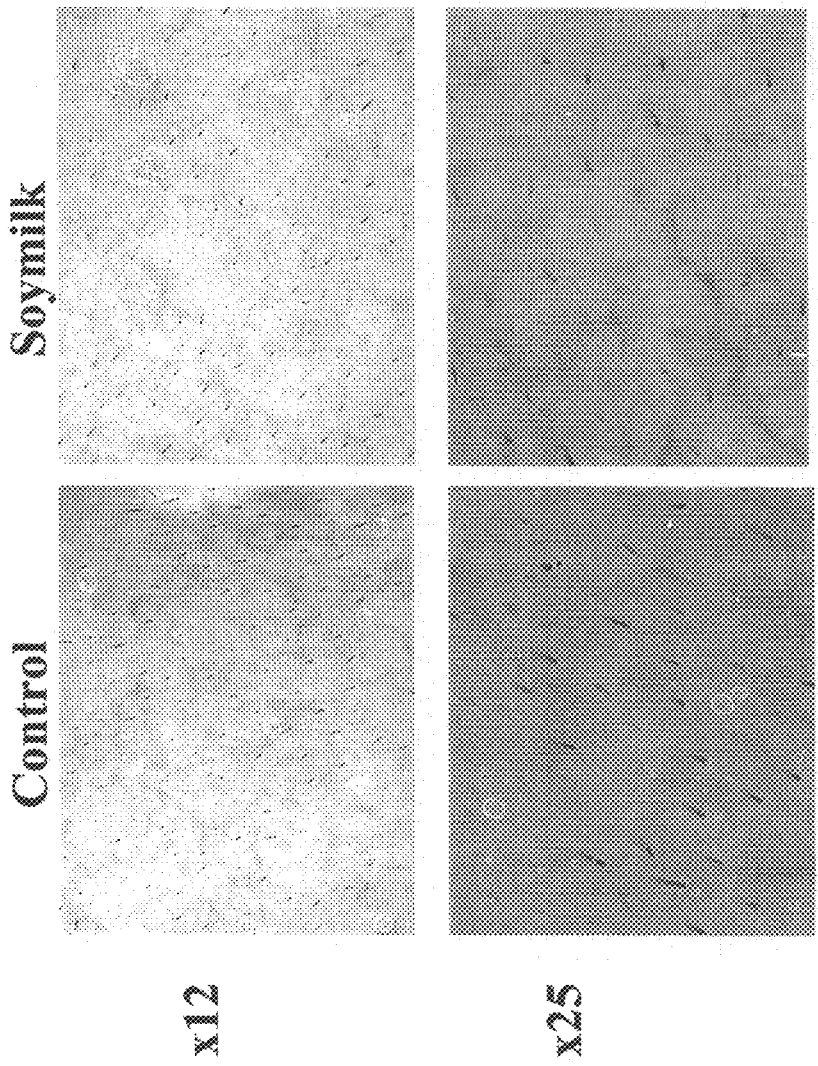
FIG. 13: Photographs of untreated and soymilk treated sides of human face, treated with soymilk daily for four weeks.

An individual male with dark facial hair who shaves daily was treating the right side of his face with soymilk, immediately after shaving, for five weeks. By the third week, and more noticeably by the forth week, the hair of the treated side was visually lighter and felt smoother to touch. Digital pictures at different magnifications were taken throughout the treatment period, using Hi-Scope. These pictures clearly demonstrate the reduced size and thickness of the hair shafts at the treated side. An example of such pictures is shown in FIG. 13, demonstrating the difference in hair shaft thickness and density at four weeks of treatment. Since both sides of the face were shaved at the same time, and pictures of both sides were taken at the same time, the difference in length of the facial hair indicates slower growth rate at the treated area.

Figure 14:
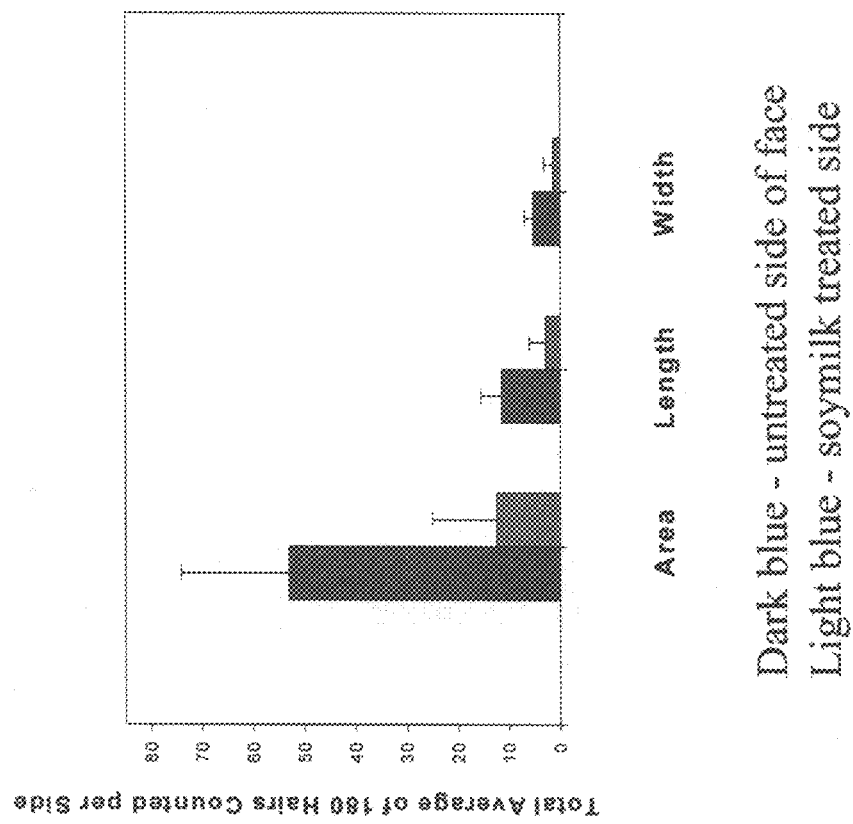
FIG. 14: Quantitative analysis of hair follicle dimensions with and without soymilk treatment.

FIG. 14 shows a computerized image analysis of the facial hair length, thickness and total area, following four weeks of soymilk treatment. All images were analyzed with Image Pro Plus 3.0 software (Media Cybernetics, Silver Spring, MD). Data are presented as average of 180 hair shafts of each side of the face, with standard deviation (SigmaPlot® 5.0, SPSS Science, Chicago, Ill.). Statistical analysis was performed using SigmaStat® 2.0 (SPSS Science) software, demonstrating a statistical significant difference in all measured parameters, following soymilk treatment.

Example 9

Soymilk Reduces Human Legs Hair Length and Thickness

Figure 15:
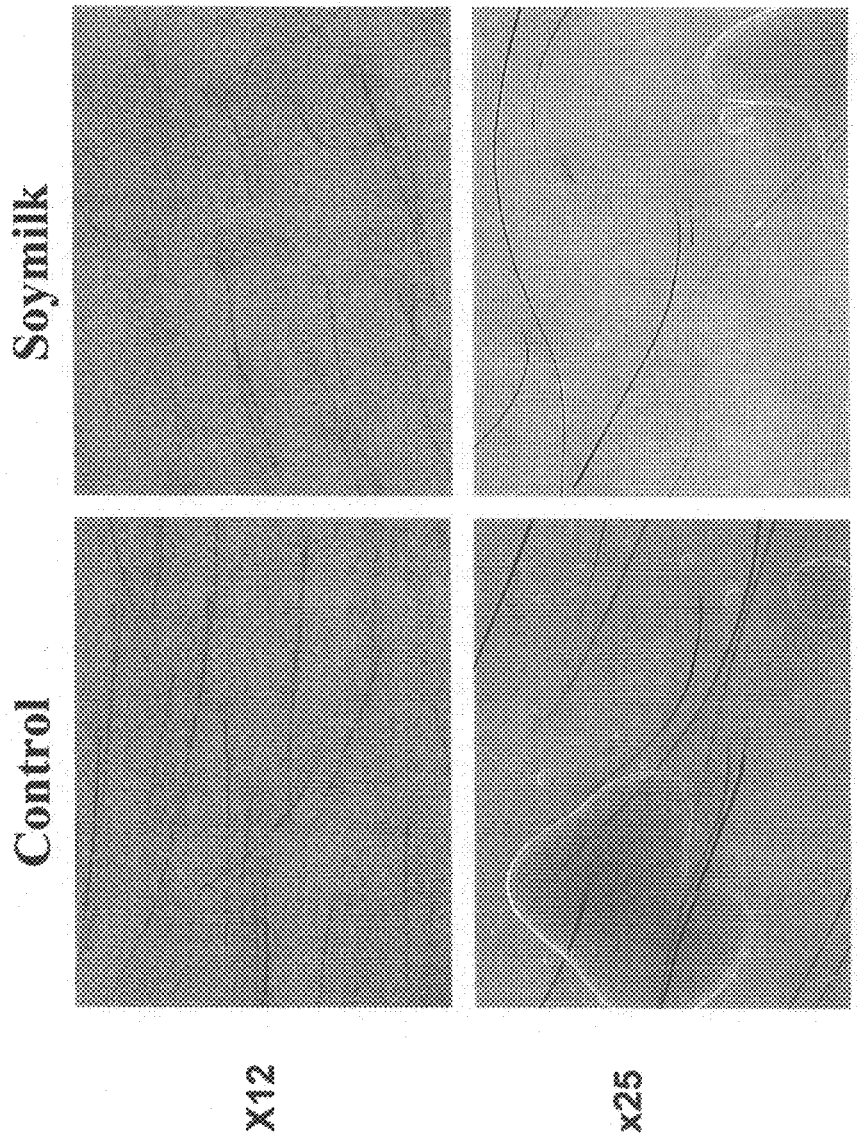
FIG. 15: Photographs of human leg hair following five weeks of soymilk treatment on one leg.

Hair was wax-depilated of two symmetrical areas of the medial part of the legs, below the knee, in one individual. One leg was treated daily, for four weeks, with soymilk. Visual observations indicate slower hair growth on the treated site. Hair shafts were reduced in number and were shorter and thinner than those of the untreated site, as shown in FIG. 15. These observations further confirm the effect of soymilk on hair growth. Examples 8 and 9 together confirm that the effect of soymilk on human hair growth is not related to the method of hair removal or to the body part being treated.

Example 10

Figure 16:
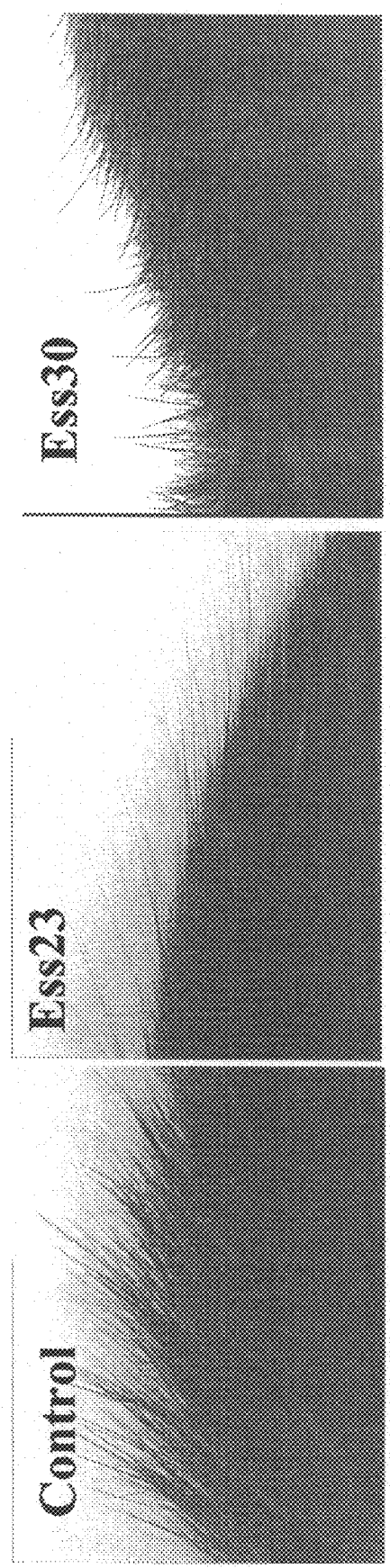
FIG. 16: Photographs of control, soymilk, and isoflavone-enriched soymilk treated C57Bl/6 mouse hair (high magnification).
Figure 17:
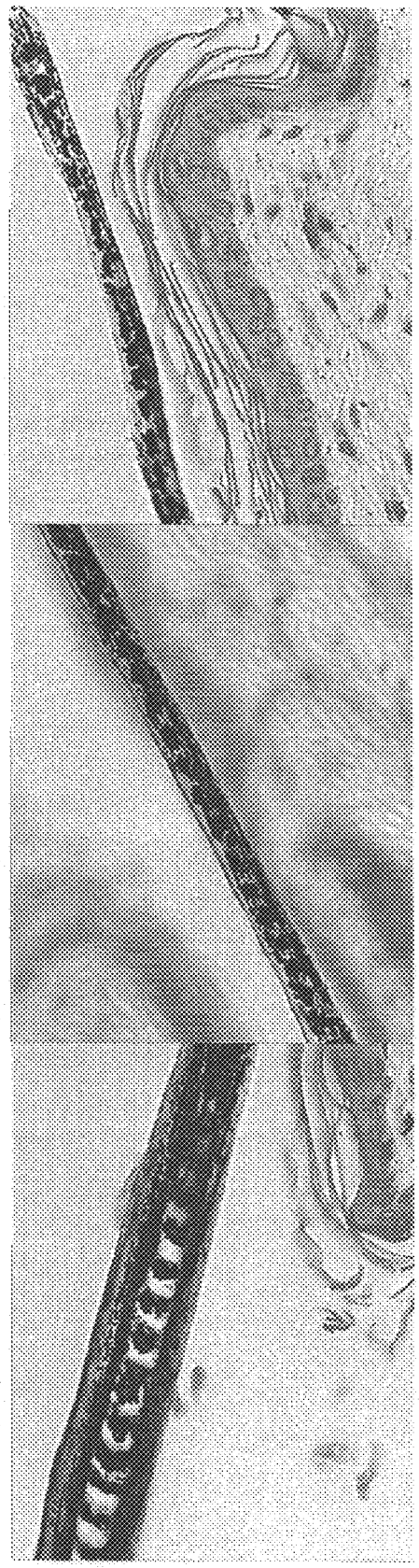
FIG. 17: Histological sections of control, soymilk, and isoflavone-enriched soymilk treated C57Bl/6 mouse skins at day 15 of the hair cycle, documenting the thickness and color of the hair shafts.

Soymilk Formulations Enriched with Isoflavones are Preferred to Soymilk Formulations in Reducing Hair Growth and Pigmentation The experiments described in Example 4 were repeated, using two formulations described in Table 2 above, Soymilk Essence 23 which is a soymilk-based formulation, and soymilk Essence 30 which is identical to Soymilk Essence 23 except the addition of 5% of a 0.1% isoflavones extract. As shown in FIG. 16, mice treated with Soymilk essence 23 show reduced hair growth and nicer hair appearance. This effect was more pronounced with the use of soymilk Essence 30, demonstrating that isoflavone-enriched soymilk formulations are superior to soymilk formulations in reducing hair growth. FIG. 17 shows histological skin sections of the treated mice, at day 15 of the treatment. The hair shafts documented in these sections clearly demonstrate the reduction in hair shaft dimensions, the reduced level of pigmentation within the hair shaft, and the increased smoothness of the hair shaft following the Soymilk Essence treatments.

Example 11

Soymilk Formulations Enriched with Isoflavones are Preferred to Isoflavone Formulations Which are Effective in Reducing Hair Growth and Pigmentation.

The experiments described in Example 4 were repeated, using formulations described in Table 2 above, of soymilk essence with or without increasing concentrations of isoflavones. These Soy Essence formulations were compare to similar formulations, where the soymilk component only was replaced with water.

These three sets of formulations (Soy Essence, isoflavones, Soy Essence containing additional isoflavones) were prepared to test the possibility that isoflavones might be sufficient for the effect observed on hair growth. FIG. 18 shows the C57Bl/6 mouse hair following three weeks of topical treatment, as described in example 4. Both untreated control mice and placebo treated mice have long and less "ordered" hair. Soymilk Essence 23 reduces hair growth and leads to a nicer appearance, as described earlier in this application.

Soymilk Essence formulations containing 1, 5 and 10% of a 0.1% isoflavones containing extract result in a superior effect on hair growth. However, formulations containing isoflavones but no soymilk demonstrate milder, and not as superior effect as when combined with soymilk. This example demonstrates that soymilk formulations containing isoflavone could reduce hair growth. This example further demonstrates that soymilk formulations containing isoflavones reduce hair growth to a higher degree than formulations containing isoflavones alone.

Example 12

Soy Essence Formulations Affect Human Hair Growth

The efficacy and irritancy potential of Soymilk Essence 23 and 30 compared to a placebo formulation were examined in a blinded placebo-controlled four-week test with twelve premenopausal female panelists ages 29 to by evaluations by the study investigator, self-assessment by panelists and Hi-scope image analysis. Panelists signed an Informed Consent and were instructed about study procedures and expectations and were asked to shave that night. At the baseline visit the following day, two test lotions were distributed to each panelist (Day 1), a placebo lotion and either soymilk Essence 23 or 30. The lotions were randomly assigned to either the right leg or left leg. The test lotions and placebo were used on the respective legs for the duration of the study with no other lotions used on the lower legs. Panelists were instructed to apply the test lotions twice daily, morning and evenings and were also instructed to try to refrain from shaving their lower legs until after each weekly evaluation. On evaluation days, the investigator visually inspected the panelists' legs for any clinical signs of irritation and compared legs for hair growth attenuation. Self-assessment questionnaires were completed by panelists at each evaluation time point (Weeks 1, 2, 3 and 4). In addition, Hi-scope images (2.5 cm in diameter for each image, KH-2400R, Hirox) were obtained at each time point using a MX-MACROZ lens (Hirox).

No panelists dropped from the study for any product-related reason. No signs of irritation were seen in any of the study panelists at any time point, nor was any irritation reported when self-assessed by panelists at any time point during the study.

For the purpose of hair counts all hair, including "stubble", were counted in the given 2.5 cm field for each panelist at each time point. Results showed a decrease in lower leg hair counts by week 5 for Soymilk Essence 30 and by week 4 for Soymilk Essence 23. The placebo treated legs did not show a change in mean leg hair counts throughout the study although the standard deviations were large. The growth rate was calculated by dividing the length of time (in days) since the panelist last shaved, by the average length of leg hairs for that panelist, which was calculated from the hi-scope images using Image Pro Plus analysis for each panelist at each test site. The results are documented in Table 3, demonstrating that both Soymilk Essences 23 and 30 treatments resulted in reduced hair growth rate compared to placebo.

TABLE 3

Mean leg hair growth rates following Soymilk Essence or placebo treatment

| Week | Location | Soymilk Essence 30 | Soymilk Essence 23 | Placebo |
| --- | --- | --- | --- | --- |
| 0 (baseline) | Upper | 0.211 (±0.07) | 0.184 (±0.07) | 0.243 (±0.07) |
|  | Lower | 0.248 (±0.08) | 0.191 (±0.06) | 0.235 (±0.09) |
| 1 | Upper | 0.216 (±0.05) | 0.153 (±0.03) | 0.211 (±0.06) |
|  | Lower | 0.178 (±0.08) | 0.213 (±0.03) | 0.188 (±0.07) |
| 2 | Upper | 0.232 (±0.11) | 0.181 (±0.04) | 0.221 (±0.07) |
|  | Lower | 0.236 (±0.12) | 0.195 (±0.07) | 0.217 (±0.09) |
| 3 | Upper | 0.241 (±0.06) | 0.185 (±0.09) | 0.285 (±0.13) |
|  | Lower | 0.213 (±0.10) | 0.147 (±0.04) | 0.253 (±0.12) |
| 4 | Upper | 0.234 (±0.07) | 0.209 (±0.11) | 0.211 (±0.09) |
|  | Lower | 0.194 (±0.05) | 0.208 (±0.07) | 0.220 (±0.04) |

Results from panelists' self-assessment questionnaires showed that panelists felt that the test lotions attenuated hair growth and softened the feel of leg hair, compared to the placebo lotion. Panelists felt that the hair felt less coarse and less stubbley. The majority of the panelists believed that the test lotions were attenuating leg hair growth or altering the texture of the hair so that it felt smoother and less coarse. Hi Scope analysis further demonstrated that the hair re-growth following treatment with Soymilk Essence 23 or 30 seemed to be growing in the same direction and was more uniform in shape, texture and appearance. In contrast, the hair that re-grew on the placebo-treated legs grew in different directions, differing in length, angle of growth and thickness.

This Example clearly demonstrate the effect of soymilk formulations in delaying and reducing hair growth, and enabling the growth of softer, less coarse and more managed and directionally-organized hair.

We claim:

1. A method of reducing hair growth and reducing hair follicles and hair shaft size in mammalian hair in need thereof, comprising topically applying at least once daily for at least seven days from the beginning of a hair cycle to hair follicles on the skin of a mammal an effective amount of a hair growth-reducing and hair follicle and shaft size reducing topically active composition comprising one or more compounds derived from one or more of a botanical family leguminosae, wherein said compounds comprise at least one serine protease inhibitor consisting essentially of soybean trypsin inhibitor, wherein after daily application for at least seven days from the beginning of the hair cycle, hair growth, hair follicles and hair shaft size are reduced in comparison with the appearance of hair prior to applying said composition.

2. The method of claim 1 wherein said at least one serine protease inhibitor is present in an amount, based upon the total volume of the topically active composition, of from about 0.0001% (w/v) to 20% (w/v).

3. The method of claim 2 wherein the at least one serine protease inhibitor is present in an amount, based upon the total volume of the topically active composition, of from about 0.001% (w/v) to about 5% (w/v).

4. The method of claim 1 wherein one of said changes is a delay in hair growth, reduced hair follicle and hair shaft size and reduced hair pigmentation.

5. The method of claim 1 wherein said topically active composition further comprises a pharmaceutically or cosmetically acceptable vehicle.

6. The method of claim 1 wherein said topically active composition further comprises one or more isoflavones.

7. The method of claim 6 wherein said topically active composition further comprises a pharmaceutically or cosmetically acceptable vehicle.

8. The method of claim 1 wherein said topically active compositions further comprises natural extracts containing one or more isoflavones.

9. The method of claim 1 wherein said composition is applied topically in conjunction with one or more products whose purpose is to either facilitate the removal of hair or actually remove hair or reduce hair visibility or improve hair style or improve hair management.

10. The method of claim 1 wherein said composition is applied topically, before or following hair removal.

11. The method of claim 1 wherein said composition is applied topically during hair removal.

12. The method of claim 1 wherein said composition is applied topically in conjunction with one or more of the group consisting of: depilatory agents, shampoo, hair conditioner, styling gel, hair care products, waxing products, shaving products, hair-removal products, after-shave products, deodorant, anti-perspirant, laser hair removal light induced hair removal, mask, and bath additives.

13. The method of claim 1 further comprising leaving said composition on said skin for a period sufficient to effect changes.

14. The method of claim 1 wherein said period is a daily treatment for at least four weeks.

15. A method according to claim 14 wherein said composition is applied daily for at least eight weeks.

16. A method according to claim 1 wherein said composition is applied daily to the axillary area to reduce hair growth.

17. A method according to claim 1 wherein said composition is added daily to a bath such that the water in said bath contacts the skin and hair follicles of a mammal.

18. A method for inhibiting mammalian hair growth of hair in need thereof, comprising applying topically to hair follicles of a mammal, at least once daily for at least seven days from the beginning of a hair growth cycle an effective amount of a hair growth inhibiting topically active agent such that it penetrates into hair follicles on the skin of a mammal, said topically active agent comprising extract of soybeans having soy trypsin inhibitory activity, wherein after such application, hair growth is reduced and hair follicle and hair shaft size are reduced in comparison with the appearance of hair prior to applying said composition.

19. A method according to claim 18 wherein said composition is applied to said hair for at least seven days from the beginning of the hair cycle.

20. A method according to claim 18 wherein said composition is applied to said hair follicle for at least seven days from the beginning of the hair cycle.

21. A method for reducing hair follicle and hair shaft size of mammalian hair in need thereof, comprising applying topically to hair follicles of a mammal, at least once daily for at least seven days from the beginning of a hair growth cycle an effective amount of a hair follicle and hair shaft size reducing topically active agent such that it penetrates into hair follicles on the skin of a mammal, said topically active agent comprising extract of soybeans having soy trypsin inhibitory activity, wherein after such application, hair follicle and hair shaft size are reduced in comparison with the appearance of hair prior to applying said composition.

22. A method for reducing hair pigmentation of mammalian hair in need thereof, comprising applying topically to hair follicles of a mammal, at least once daily for at least seven days from the beginning of a hair growth cycle an effective amount of a hair pigmentation reducing topically active agent such that it penetrates into hair follicles on the skin of a mammal, said topically active agent comprising extract of soybeans having soy trypsin inhibitory activity, wherein after such application, hair pigmentation is reduced, hair growth is reduced and hair follicle and hair shaft size are reduced in comparison with the appearance of hair prior to applying said composition.

23. A method according to claim 22 wherein said composition is applied to said hair for at least seven days from the beginning of the hair cycle.

24. A method of reducing hair pigmentation, reducing hair growth, reducing hair follicles and reducing hair shaft size in mammalian hair in need thereof, comprising topically applying to hair follicles of a mammal, at least once daily for at least seven days from the beginning of a hair growth cycle an effective amount of a hair pigmentation, hair growth, hair follicle and hair shaft size reducing topically active composition comprising one or more compounds derived from soybeans having soy trypsin inhibitory activity wherein said compound consists essentially of soybean trypsin inhibitor wherein after such application, hair pigmentation is reduced, hair growth is reduced and hair follicle and hair shaft size are reduced in comparison with the appearance of hair prior to applying said composition.

25. A method according to claim 24 wherein said composition is applied to said hair follicles for at least seven days from the beginning of the hair cycle.

26. A method of reducing pseudofolliculitis barbae in mammalian hair in need thereof, comprising applying topically to hair follicles of a mammal, at least once daily for at least seven days from the beginning of a hair growth cycle, an effective amount of a hair growth-reducing and hair follicle and shaft size-reducing topically active composition comprising one or more compounds derived from one or more of a botanical family leguminosae, wherein said compounds contain at least one serine protease inhibitor consisting essentially of soybean trypsin inhibitor, wherein after daily application for at least seven days from the beginning of the hair cycle, hair growth, hair follicle and hair shaft size are reduced in comparison with the appearance of hair prior to applying said composition.

27. A method to style and improve management of African type hair in mammalian hair in need thereof, comprising applying topically to hair follicles of a mammal, at least once daily for at least seven days from the beginning of a hair cycle an effective amount of a hair growth-reducing and hair follicle and shaft size-reducing topically active composition comprising one or more compounds derived from one or more of a botanical family leguminosae, wherein said compounds contain at least one serine protease inhibitor consisting essentially of soybean trypsin inhibitor, wherein after daily application for at least seven days from the beginning of the hair cycle, management of African type hair is improved in comparison with the appearance of hair prior to applying said composition.

28. A method to for delaying hair growth and reducing hair visibility in sufferers of hirsutism, comprising applying topically to hair follicles of a mammal, at least once daily for at least seven days from the beginning of a hair cycle to hair on the skin of a sufferer of hirsutism an effective amount of a hair growth-reducing and hair follicle and shaft size-reducing topically active composition comprising one or more compounds derived from one or more of a botanical family leguminosae, wherein said compounds contain at least one serine protease inhibitor consisting essentially of soybean trypsin inhibitor, wherein after daily application for at least seven days from the beginning of the hair cycle, hair growth is delayed and hair visibility in sufferers of hirsutism is reduced in comparison with the appearance of hair prior to applying said composition.

29. A method of reducing hair growth and reducing hair follicles and hair shaft size in mammalian hair in need thereof, comprising topically applying at least once daily for at least seven days from the beginning of a hair cycle to hair on the skin of a mammal an effective amount of a hair growth-reducing and hair follicle and shaft size-reducing topically active composition comprising one or more compounds derived from one or more of a botanical family leguminosae, wherein said compounds comprise at least one serine protease inhibitor consisting essentially of soybean trypsin inhibitor and Bowman-Birk Inhibitor, wherein after daily application for at least seven days from the beginning of the hair cycle, hair growth, hair follicle and hair shaft size are reduced in comparison with the appearance of hair prior to applying said composition.

30. A method of reducing hair growth and reducing hair follicles and hair shaft size in mammalian hair in need thereof, comprising topically applying at least once daily for at least seven days from the beginning of a hair cycle to hair follicles on the skin of a mammal an effective amount of a hair growth-reducing and hair follicle and shaft size reducing topically active composition consisting essentially of soybean trypsin inhibitor, wherein after daily application for at least seven days from the beginning of the hair cycle, hair growth, hair follicles and hair shaft size are reduced in comparison with the appearance of hair prior to applying said composition.

* * * * *